US012558392B1

(12) United States Patent
Tran

(10) Patent No.: US 12,558,392 B1
(45) Date of Patent: Feb. 24, 2026

(54) HERBAL ORAL COMPOSITIONS HAVING THE PROPERTIES FOR SUPPORTING AND ENHANCING MUSCULOSKELETAL HEALTH AND METHOD OF MANUFACTURING THE SAME

(71) Applicant: Dang Huy Tran, Ho Chi Minh (VN)

(72) Inventor: Dang Huy Tran, Ho Chi Minh (VN)

(73) Assignee: Dang Huy Tran, Ho Chi Minh (VN)

( * ) Notice: Subject to any disclaimer, the term of this patent is extended or adjusted under 35 U.S.C. 154(b) by 0 days.

(21) Appl. No.: 19/277,384

(22) Filed: Jul. 23, 2025

Related U.S. Application Data

(63) Continuation of application No. 19/275,921, filed on Jul. 21, 2025.

(51) Int. Cl.

| | |
|---|---|
| *A61K 36/67* | (2006.01) |
| *A61K 9/00* | (2006.01) |
| *A61K 31/05* | (2006.01) |
| *A61K 31/685* | (2006.01) |
| *A61K 31/704* | (2006.01) |
| *A61K 31/722* | (2006.01) |
| *A61K 36/07* | (2006.01) |
| *A61K 36/076* | (2006.01) |
| *A61K 36/185* | (2006.01) |
| *A61K 36/19* | (2006.01) |
| *A61K 36/21* | (2006.01) |
| *A61K 36/232* | (2006.01) |
| *A61K 36/236* | (2006.01) |
| *A61K 36/238* | (2006.01) |
| *A61K 36/268* | (2006.01) |
| *A61K 36/282* | (2006.01) |
| *A61K 36/287* | (2006.01) |
| *A61K 36/31* | (2006.01) |
| *A61K 36/33* | (2006.01) |
| *A61K 36/42* | (2006.01) |
| *A61K 36/46* | (2006.01) |
| *A61K 36/484* | (2006.01) |
| *A61K 36/53* | (2006.01) |
| *A61K 36/54* | (2006.01) |

(Continued)

(52) U.S. Cl.
CPC ............ *A61K 36/67* (2013.01); *A61K 9/0053* (2013.01); *A61K 31/05* (2013.01); *A61K 31/685* (2013.01); *A61K 31/704* (2013.01); *A61K 31/722* (2013.01); *A61K 36/07* (2013.01); *A61K 36/076* (2013.01); *A61K 36/185* (2013.01); *A61K 36/19* (2013.01); *A61K 36/21* (2013.01); *A61K 36/232* (2013.01); *A61K 36/236* (2013.01); *A61K 36/238* (2013.01); *A61K 36/268* (2013.01); *A61K 36/282* (2013.01); *A61K 36/287* (2013.01); *A61K 36/31* (2013.01); *A61K 36/33* (2013.01); *A61K 36/42* (2013.01); *A61K 36/46* (2013.01); *A61K 36/484* (2013.01); *A61K 36/53* (2013.01); *A61K 36/54* (2013.01); *A61K 36/59* (2013.01); *A61K 36/64* (2013.01); *A61K 36/65* (2013.01); *A61K 36/79* (2013.01); *A61K 36/88* (2013.01); *A61K 38/39* (2013.01); *A61K 47/02* (2013.01); *A61K 47/12* (2013.01); *A61K 47/14* (2013.01); *A61K 47/26* (2013.01); *A61K 47/34* (2013.01); *A61K 47/36* (2013.01); *A61P 19/02* (2018.01); *A61K 2236/13* (2013.01); *A61K 2236/15* (2013.01); *A61K 2236/17* (2013.01); *A61K 2236/19* (2013.01); *A61K 2236/331* (2013.01); *A61K 2236/39* (2013.01); *A61K 2236/51* (2013.01); *A61K 2236/53* (2013.01)

(58) Field of Classification Search
CPC ...... A61K 36/67; A61K 9/0053; A61K 31/05; A61K 31/685; A61K 31/704; A61K 31/722; A61K 36/07; A61K 36/076; A61K 36/185; A61K 36/19; A61K 36/21; A61K 36/232; A61K 36/236; A61K 36/238; A61K 36/268; A61K 36/282; A61K 36/287; A61K 36/31; A61K 36/33; A61K 36/42; A61K 36/46; A61K 36/484; A61K 36/53; A61K 36/54; A61K 36/59; A61K 36/64; A61K 36/65; A61K 36/79; A61K 36/88; A61K 38/39; A61K 47/02; A61K 47/12; A61K 47/14; A61K 47/26; A61K 47/34; A61K 47/36; A61K 2236/13; A61K 2236/15; A61K 2236/17; A61K 2236/19; A61K 2236/331; A61K 2236/39; A61K 2236/51; A61K 2236/53; A61P 19/02
See application file for complete search history.

(56) References Cited

U.S. PATENT DOCUMENTS

2009/0104295 A1* 4/2009 Kohno ..................... A61Q 7/00
424/757

OTHER PUBLICATIONS

Organisation for Economic Co-Operation and Development. Test No. 425: Acute Oral Toxicity: Up-and-Down Procedure. OECD Publishing, 2008.

(Continued)

*Primary Examiner* — Aaron J Kosar

(57) ABSTRACT

A herbal oral composition having the properties for supporting and enhancing musculoskeletal health and processes for manufacturing the same from ingredients are disclosed comprising: a herbal concentrate having a first predetermined percentage (%) by weight, a herbal powder mixture having a second predetermined percentage (%) by weight, a mushroom extract ingredient having a third predetermined percentage (%) by weight, a collagen extract ingredient having a fourth percentage (%) by weight, a solution containing 4-allylpyrocatechol having a fifth percentage (%) by weight, and a plant-derived nanovesicles ingredient having a sixth percentage (%) by weight.

15 Claims, 1 Drawing Sheet

(51) Int. Cl.

| | |
|---|---|
| *A61K 36/59* | (2006.01) |
| *A61K 36/64* | (2006.01) |
| *A61K 36/65* | (2006.01) |
| *A61K 36/79* | (2006.01) |
| *A61K 36/88* | (2006.01) |
| *A61K 38/39* | (2006.01) |
| *A61K 47/02* | (2006.01) |
| *A61K 47/12* | (2006.01) |
| *A61K 47/14* | (2017.01) |
| *A61K 47/26* | (2006.01) |
| *A61K 47/34* | (2017.01) |
| *A61K 47/36* | (2006.01) |
| *A61P 19/02* | (2006.01) |

(56) References Cited

OTHER PUBLICATIONS

Pritzker K.P., Gay S., Jimenez S.A., et al., Osteoarthritis cartilage histopathology: grading and staging, Osteoarthritis and Cartilage, 14(1), pp. 13-29, 2006.

* cited by examiner

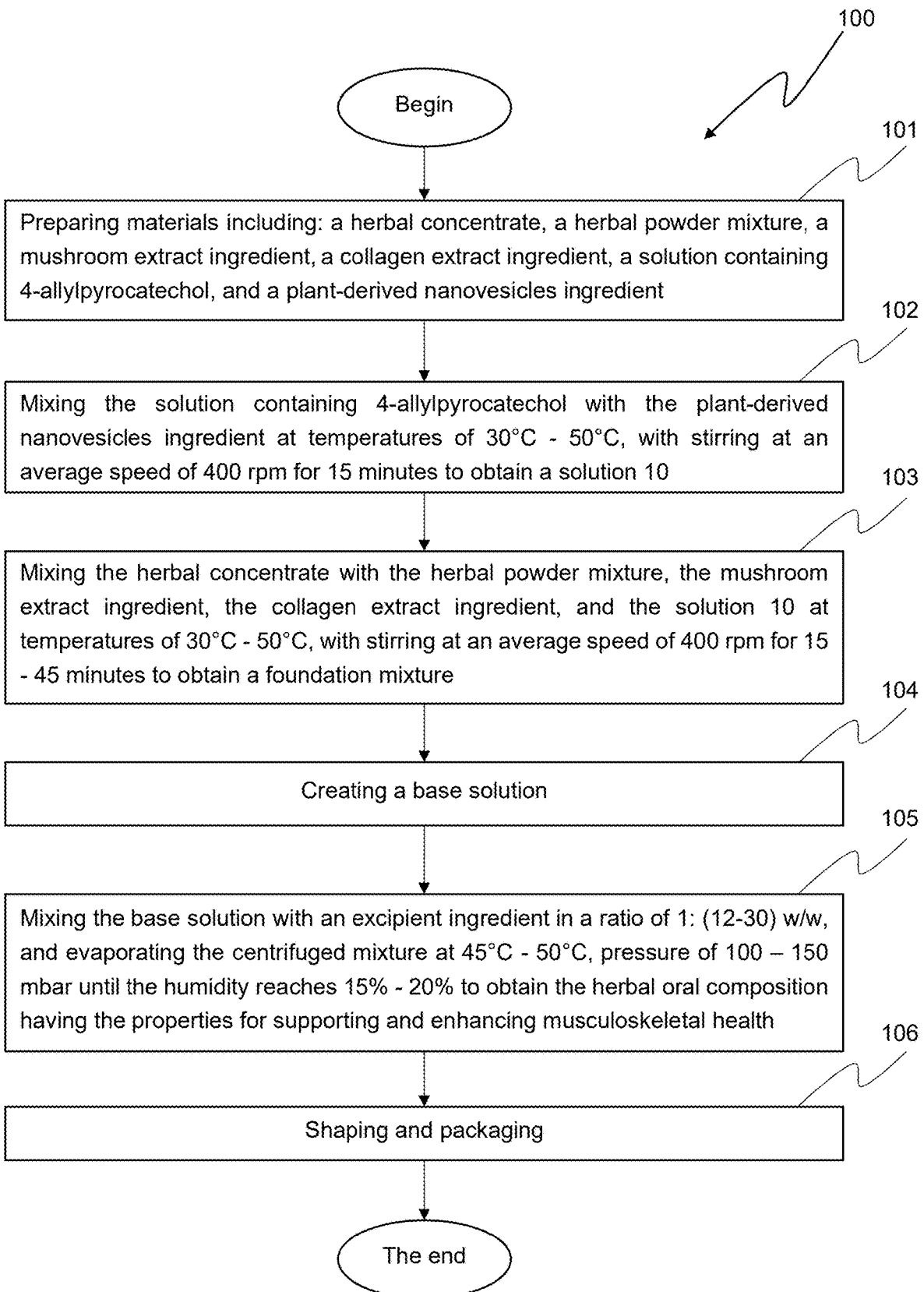

HERBAL ORAL COMPOSITIONS HAVING THE PROPERTIES FOR SUPPORTING AND ENHANCING MUSCULOSKELETAL HEALTH AND METHOD OF MANUFACTURING THE SAME

CLAIM OF PRIORITY

This application is a continuation application of application Ser. No. 19/275,921, entitled "Plant-based extract complex composition having the properties for supporting the relief of musculoskeletal pain, antibacterial and anti-inflammatory and process of manufacturing the same", filed on 21 Jul. 2025. The patent application identified above is incorporated here by reference in its entirety to provide continuity of disclosure.

FIELD OF THE INVENTION

The present invention relates to the field of herbal pharmaceutical formulations for musculoskeletal health. More specifically, it relates to a multi-component oral composition combining standardized herbal and mushroom extracts, marine collagen, betel leaf-derived 4-allylpyrocatechol, and plant-derived nanovesicles to alleviate inflammation and support joint function. The invention further encompasses the method and integrated manufacturing process steps for preparing this bioactive composition.

BACKGROUND ART

The musculoskeletal system is frequently compromised by chronic inflammatory and degenerative conditions, such as osteoarthritis, rheumatoid arthritis, and age-related cartilage deterioration, that result in pain, reduced mobility, and diminished quality of life. Conventional treatments predominantly involve nonsteroidal anti-inflammatory drugs (NSAIDs) and synthetic analgesics to manage symptoms; however, prolonged NSAID use is associated with gastrointestinal, renal, and cardiovascular side effects, and these interventions often fail to halt or reverse tissue degeneration. In recent years, there has been growing interest in nutraceutical and herbal approaches that offer anti-inflammatory and chondroprotective benefits without the adverse side-effect profiles of synthetic drugs.

A variety of single-entity herbal extracts have been investigated for joint health, including *Angelica pubescens, Cinnamomum cassia, Asarum heterotropoides*, and *Ligusticum wallichii*, each demonstrating variable degrees of anti-inflammatory, analgesic, or antioxidative activity. Yet standardized bioactive compound concentrations are difficult to maintain across batches, leading to inconsistent clinical outcomes. Similarly, mushroom-derived β-glucan preparations (e.g., from *Auricularia auricula, Tremella fuciformis, Lentinus edodes, Hericium erinaceus*) have been shown to modulate immune responses and support cartilage health, but these extracts often suffer from low oral bioavailability due to high molecular weight and poor solubility. Marine collagen, particularly low-molecular-weight fractions obtained from fish byproducts, has demonstrated promise in promoting cartilage matrix synthesis and reducing joint stiffness, but its rapid enzymatic degradation in the gastrointestinal tract limits systemic delivery to the joint microenvironment.

4-Allylpyrocatechol (APC), a phenolic compound isolated from *Piper betle* (betel leaf), exhibits potent anti-inflammatory and antioxidant properties in preclinical studies; however, APC's clinical translation is hindered by its poor stability in the gastric milieu and rapid first-pass metabolism, leading to subtherapeutic levels at the site of inflammation. While liposomal and synthetic polymer-based nanoparticle carriers have been explored for phytochemical delivery, these systems often involve synthetic excipients that may trigger immunogenicity or accumulate in vivo. In contrast, plant-derived nanovesicles (PDNVs) have recently emerged as a biocompatible platform capable of protecting sensitive phytochemicals, enhancing mucosal uptake, and enabling targeted delivery without adverse immunological consequences.

Existing formulations in the marketplace rarely integrate multiple bioactive modalities, such as standardized herbal concentrates, mushroom extracts, marine collagen, purified APC, and PDNVs, into a single, cohesive, and scalable manufacturing process. Those that do often lack synergistic optimization, leading to suboptimal efficacy. Moreover, no current oral composition has successfully demonstrated simultaneous protection of APC through PDNV encapsulation, stabilization of marine collagen, and co-release of polysaccharide, phenolic, and proteinaceous actives in a consistent, reproducible manner. As a result, there exists a clear need for a multi-component oral pharmaceutical herbal composition engineered to overcome bioavailability challenges, synchronize release profiles, and harness synergistic interactions among phytochemicals, β-glucans, collagen peptides, and nanovesicular carriers to maximize anti-inflammatory and regenerative effects for musculoskeletal health.

The invention aims to solve these technical problems of the prior art by providing a herbal oral composition having the properties for supporting and enhancing musculoskeletal health comprising: a herbal concentrate having a first predetermined percentage (%) by weight, a herbal powder mixture having a second predetermined percentage (%) by weight, a mushroom extract ingredient having a third predetermined percentage (%) by weight, a collagen extract ingredient having a fourth percentage (%) by weight, a solution containing 4-allylpyrocatechol having a fifth percentage (%) by weight, and a plant-derived nanovesicles ingredient having a sixth percentage (%) by weight.

In particular, the objective of the present invention is to provide a method of manufacturing a herbal oral composition having the properties for supporting and enhancing musculoskeletal health comprising: (i) preparing materials including: a herbal concentrate, a herbal powder mixture, a mushroom extract ingredient, a collagen extract ingredient, a solution containing 4-allylpyrocatechol, and a plant-derived nanovesicles ingredient; (ii) mixing the solution containing 4-allylpyrocatechol with the plant-derived nanovesicles ingredient to obtain a solution 10; (iii) mixing the herbal concentrate with the herbal powder mixture, the mushroom extract ingredient, the collagen extract ingredient, and the solution 10 to obtain a foundation mixture; (iv) creating a base solution; (v) mixing the base solution with an excipient ingredient to obtain the herbal oral composition having the properties for supporting and enhancing musculoskeletal health; and (vi) shaping and packaging.

Finally, what is needed is a manufacturing process featuring simplified operational steps, optimized technical specifications, and the potential for seamless scale-up to industrial production.

This invention provides solutions to achieve the above goals by integrating compatible extraction, concentration, and mixing protocols into a unified, reproducible workflow.

SUMMARY OF THE INVENTION

This present invention provides, in one aspect, a herbal oral composition for the alleviation of the symptoms associated with arthritis or herbal oral composition for the prophylactic amelioration of arthritis. The present composition also provides methods of extracting useful compounds from herbs for use in these oral composition.

Accordingly, an objective of the present invention is to provide a method of manufacturing a herbal oral composition having the properties for supporting and enhancing musculoskeletal health, comprising the following steps (i) to (vi):

(i) preparing materials including: a herbal concentrate having a first predetermined percentage (%) by weight, a herbal powder mixture having a second predetermined percentage (%) by weight, a mushroom extract ingredient having a third predetermined percentage (%) by weight, a collagen extract ingredient having a fourth percentage (%) by weight, a solution containing 4-allylpyrocatechol having a fifth percentage (%) by weight, and a plant-derived nanovesicles ingredient having a sixth percentage (%) by weight;

(ii) mixing the solution containing 4-allylpyrocatechol with the plant-derived nanovesicles ingredient at temperatures of 30° C.-50° C., with stirring at an average speed of 400 rpm for 15 minutes to obtain a solution 10;

(iii) mixing the herbal concentrate with the herbal powder mixture, the mushroom extract ingredient, the collagen extract ingredient, and the solution 10 at temperatures of 30° C.-50° C., with stirring at an average speed of 400 rpm for 15-45 minutes to obtain a foundation mixture;

(iv) creating a base solution, wherein 100 mL of the base solution created by mixing performed in a specific order from (h1) to (h3) comprising:

(h1) adding 125 mg of the foundation mixture with 100 mg of glycyrrhizic acid, 50 mg of a phospholipid component, and 315 mg of lipoid S100 into a reaction tank, adding 0.2 part of absolute ethanol, refluxing at 60° C. for 2 hours to obtain a solution 20;

(h2) dissolving 250 mg of chitosan with 10 mL of distilled water, slowly adding 0.5 mL of glacial acetic acid, combined with stirring 50 rpm, adding 30 ml of water and let stand until the solution is clear, transferring the cleared solution into a 50 mL volumetric flask, and adding distilled water to the mark to obtain 50 mL of a chitosan solution with concentration of 5 mg/mL; and (h3) dissolving 1 mL of the chitosan solution at step (h2) with 300 mg of a poloxamer component and 85 mL of distilled water, cooling the reaction mixture and stirring at 600 rpm until the reaction mixture is homogeneous, injecting 8 mL of the solution 10 at a rate of 1 mL/min with a stirring speed of 1000 rpm for 30 minutes, and adding distilled water to make 100 mL of the base solution;

(v) mixing the base solution with an excipient ingredient in a ratio of 1:(12-30) w/w, and evaporating the centrifuged mixture at 45° C.-50° C., pressure of 100-150 mbar until the humidity reaches 10%-20% to obtain the herbal oral composition having the properties for supporting and enhancing musculoskeletal health; wherein the excipient ingredient is prepared by mixing corn starch, lactose, talc, nipagin, propylparaben and mag nesium stearate in the ratio of 3.5:1.5:2.5:1:1:1.5 by mass; and (vi) shaping and packaging.

Another objective of the present invention is to provide a herbal oral composition having the properties for supporting and enhancing musculoskeletal health including: a herbal concentrate having 25% to 60% by weight, a herbal powder mixture having 20% to 60% by weight, a mushroom extract ingredient having 0.5% to 18% by weight, a collagen extract ingredient having 0.1% to 20% by weight, a solution containing 4-allylpyrocatechol having 0.01% to 0.45% by weight, and a plant-derived nanovesicles ingredient having 0.02% to 0.2% by weight; wherein the composition is produced by the method of manufacturing comprising steps (i) to (iv) described in detail above.

Another objective of the present invention is to provide a herbal oral composition having the properties for supporting and enhancing musculoskeletal health including: a herbal concentrate having 30% to 60% by weight, a herbal powder mixture having 30% to 60% by weight, a mushroom extract ingredient having 1.5% to 18% by weight, a collagen extract ingredient having 2.5% to 20% by weight, a solution containing 4-allylpyrocatechol having 0.01% to 0.45% by weight, and a plant-derived nanovesicles ingredient having 0.02% to 0.2% by weight; wherein the composition is produced by the method of manufacturing comprising steps (i) to (iv) described in detail above.

These and other advantages of the present invention will no doubt become obvious to those of ordinary skill in the art after having read the following detailed description of the preferred embodiments, which are illustrated in the various drawing Figures.

BRIEF DESCRIPTION OF THE DRAWING

The accompanying drawings, which are incorporated in and form a part of this specification, illustrate embodiments of the invention and, together with the description, serve to explain the principles of the invention.

FIG. 1 is a flowchart illustrating a method of manufacturing a herbal oral composition having the properties for supporting and enhancing musculoskeletal health in accordance with an exemplary embodiment of the present invention.

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well-known methods, procedures, components, and circuits have not been described in detail so as not to unnecessarily obscure aspects of the present invention.

It should be noted that the terms "comprises" and "comprising", as well as "the" and "these", are intended to cover a non-exclusive inclusion. For example, a process, method, system, product, or device that comprises a series of steps or units is not necessarily limited to those explicitly listed and may include other steps or units not explicitly mentioned or inherent to such processes, methods, products, or devices.

In the embodiment of the present invention, percent mass or percentage (%) by weight=(mass of solute/mass of solution)×100%. The unit of mass is usually grams, or kilograms. Mass percent is also known as the correct percentage by weight or w/w %. It should also be noted that the molar mass is also within the meaning of the invention. Molar mass is the total mass of all atoms in a mole of compound. Total all volume percentages add up to 100%.

It should also be noted that the term "mixing homogenizing" is used in the invention understood to mean the uniform distribution, or complete dissolution of, substances present in a solution/mixture.

It should be noted that the terms "admixed/mixed/admixing/mixing" as used in the present invention is understood to mean adding, or reacting, or dissolving homogeneously, or evenly, components in the same solution/mixture.

As the plant extracted or herbal extracted or medicine herbal extracted in the present invention, an "extracts" extracted as an active compound contained in any of the plants mentioned. The plant extract in an active compounds sense obtained by steam distillation from the above plants or dried materials thereof is preferably used as the "extracts" in the present invention, but is not limited thereto. For example, active compounds extracted from the plants by using other methods such as extraction or expression are also included in the "extracts" of the present invention as long as they contain extracted components (such as active compounds). Other methods for extracting active compounds from plants, for example, solvent extraction (such as alcohol extraction, organic solvent extraction), oil and fat adsorption extraction (hot effleurage or cold effleurage), and supercritical fluid extraction are known. Examples of the solvent used for extraction include, but are not limited to, alcohols such as ethanol, methanol, propanol, isopropanol, and butanol, and organic solvents including relatively high polarity solvents such as acetone and low polarity solvents such as hexane. The "extracts" in the present invention may be those in which the active compounds obtained by the above method is further purified and concentrated by using various purification procedures such as hydrophobic or adsorptive chromatography using a support such as porous beads, silica gel, or alumina.

One embodiment of the invention is now described with reference to FIG. 1. FIG. 1 illustrates a flowchart illustrating a method of manufacturing a herbal oral composition having the properties for supporting and enhancing musculoskeletal health 100 ("method 100") based on the above principle in accordance with an exemplary embodiment of the present invention. In particular, method 100 includes the following steps:

At step 101, preparing materials includes the ingredients listed in Table 1 below, including: a herbal concentrate having a first predetermined percentage (%) by weight, a herbal powder mixture having a second predetermined percentage (%) by weight, a mushroom extract ingredient having a third predetermined percentage (%) by weight, a collagen extract ingredient having a fourth percentage (%) by weight, a solution containing 4-allylpyrocatechol having a fifth percentage (%) by weight, and a plant-derived nanovesicles ingredient having a sixth percentage (%) by weight.

According to the embodiment of the present invention, the herbal concentrate is prepared by performing steps (a1) to (a3), including:

(a1) collecting and pre-processing 19 types of medicine herbals to be extracted individually including removing damaged parts, washing, drying overnight and drying at 40° C.-50° C. until reaching 8%-15% moisture, chopping and stored in separate instruments;

wherein 19 types of medicine herbals from (A) to (U) listed in Table 2 below, including: *Angelica pubescens* uses the root parts, *Cinnamomum cassia* uses the branch parts, *Asarum heterotropoides* uses the root parts, *Ligusticum wallichii* uses the rhizome parts, *Angelica sinensis* uses the root parts, *Saposhnikovia divaricata* uses the root parts, *Eucommia ulmoides* uses the bark parts, *Achyranthes bidentata* uses the root parts, *Wolfiporia extensa* uses the fruiting body parts, *Glycyrrhiza uralensis* uses the root parts, *Loranthus parasiticus* uses the branch parts, *Paeonia lactiflora* uses the root parts, *Rehmannia glutinosa* uses the root parts, *Justicia gendarussa* uses the root parts, *Tinospora sinensis* uses the stem and leaves, *Chrysanthemum indicum* uses the flower, *Vitex negundo* use the leaves, *Brassica alba* uses the seed, and *Justicia gendarussa* uses the bark parts;

(a2) creating a medicine herbal mixture by mixing 19 types of medicine herbals prepared in step (a1) in the following percentage (%) by weight: 2.25 parts of *Angelica pubescens*, 1.5 parts of *Cinnamomum cassia*, 1.5 parts of *Asarum heterotropoides*, 1.5 parts of *Ligusticum wallichii*, 1.5 parts of *Angelica sinensis*, 2 parts of *Saposhnikovia divaricata*, 1.5 parts of *Eucommia ulmoides*, 2.25 parts of *Achyranthes bidentata*, 1.5 parts of *Poria cocos*, 1.5 parts of *Glycyrrhiza uralensis*, 1.5 parts of *Loranthus parasiticus*, 1.5 parts of *Paeonia lactiflora*, 1.5 parts of *Rehmannia glutinosa*, 1.5 parts of *Justicia gendarussa*, 1.2 parts of *Tinospora sinensis*, 1.2 parts of *Chrysanthemum indicum*, 0.5-1 parts of *Vitex negundo*, 0.5-1.5 parts *Brassica alba*, and 0.5-1 parts of *Justicia gendarussa*; and (a3) creating the herbal concentrate by soaking the medicine herbal mixture by mixing the medicine herbal mixture with water in a ratio of 1:15-20 w/v, extracting at 65° C.-70° C. for 3-4 hours to obtain a mixture 1, centrifuging the mixture 1 at a speed of 3000-4000 rpm for 30-40 minutes to obtain a centrifuged solution 1 and a residue 1; soaking the residue 1 with water and enzyme cellulase in a ratio of 1000:5000: (1-2) w/v/w, incubating at 45° C.-50° C. for 2-3 hours to obtain a mixture 2, centrifuging the mixture 2 at a speed of 3000-4000 rpm for 30-40 minutes to obtain a centrifuged solution 2 and a residue 2; soaking the residue 2 with ethanol 60% in a ratio of 1:10 w/v, stirring 600-700 rpm and support ultrasonic waves at frequency 0.2-0.3 kHz to obtain a mixture 3, centrifuging the mixture 3 at a speed of 3000-4000 rpm for 30-40 minutes to obtain a centrifuged solution 3 and a residue 3; mixing the centrifuged solution with the centrifuged solution 2, and the centrifuged solution 3 to obtain a centrifuged mixture; and evaporating the centrifuged mixture at 45° C.-50° C., pressure of 100-150 mbar until the humidity reaches 25%-30% to obtain the herbal concentrate.

According to the embodiment of the present invention, the herbal powder mixture is prepared by performing steps (b1) to (b2), including:

(b1) collecting and pre-processing 17 types of medicine herbals to be used individually including removing damaged parts, washing, drying overnight and drying at 40° C.-50° C. until reaching 8%-15% moisture, chopping, grinding into powder and stored in separate instruments;

wherein 17 types of medicine herbal powders from (A)-(R) listed in Table 2 below, including: *Angelica pubescens* uses the root parts, *Cinnamomum cassia* uses the branch parts, *Asarum heterotropoides* uses the root parts, *Ligusticum wallichii* uses the rhizome parts, *Angelica sinensis* uses the root parts, *Saposhnikovia divaricata* uses the root parts, *Eucommia ulmoides* uses the bark parts, *Achyranthes bidentata* uses the root parts, *Wolfiporia extensa* uses the fruiting body parts, *Glycyrrhiza uralensis* uses the root parts, *Loranthus parasiticus* uses the branch parts, *Paeonia lactiflora* uses the root parts, *Rehmannia glutinosa* uses the root parts, *Justicia gendarussa* uses the root parts, *Tinospora sinensis* uses the stem and leaves, *Brassica alba* uses the seed, and *Chrysanthemum indicum* use the flower; and (b2) creating the herbal powder mixture by admixing 17 types of medicine herbals prepared in step (b1) in the following percentage (%) by weight: 2.25 parts of *Angelica pubescens*, 1.5 parts of *Cinnamomum cassia*, 1.5 parts of *Asarum heterotropoides*, 1.5 parts of *Ligusticum wallichii*, 1.5 parts of *Angelica sinensis*, 2 parts of *Saposhnikovia divaricata*, 1.5 parts of *Eucommia ulmoides*, 2.25 parts of *Achyranthes bidentata*, 1.5 parts of *Poria cocos*, 1.5 parts of *Glycyrrhiza uralensis*, 1.5 parts of *Loranthus parasiticus*, 1.5 parts of *Paeonia lactiflora*, 1.5 parts of *Rehmannia glutinosa*, 1.5 parts of *Justicia gendarussa*, 1.2 parts of *Tinospora sinensis*, 0.5-1.5 parts *Brassica alba*, and 1.2 parts of *Chrysanthemum indicum*.

According to the embodiment of the present invention, the mushroom extract ingredient is prepared by performing steps (c1) to (c4), including:

(c1) collecting and pre-processing four types of mushrooms to be extracted individually including removing damaged parts, washing, drying at 40° C.-50° C. until reaching 8%-15% moisture, chopping, and stored in separate instruments; wherein four types of mushrooms include *Auricularia auricula*, *Tremella fuciformis*, *Lentinus edodes*, and *Hericium erinaceus*;

(c2) creating a mushroom mixture by admixing four types of mushrooms prepared in step (c1) in the following percentage (%) by weight: 1-2 parts *Auricularia auricula*, 1-2 parts *Tremella fuciformis*, 1-2 parts *Lentinus edodes*, and 1-2 parts *Hericium erinaceus*;

(c3) mixing the mushroom mixture with water, enzyme cellulase, and enzyme β-glucanase in a ratio of 1000:10000:1:1, then incubating at 45° C.-50° C. for 1 hours, and filtering to obtain a treated mushroom mixture; and (c4) grinding the treated mushroom mixture, heating at 70° C. for 2 hours, cooling and freeze-drying to obtain a freeze-dried powder, soaking the freeze-dried powder with ethanol 70% in a ratio of 9:200 w/v, supported ultrasonic waves at a frequency of 0.2-0.3 kHz for 90 minutes to obtain a temporary mixture 1, centrifuging the temporary mixture 1 at a speed of 3000-4000 rpm for 30-40 minutes to obtain a temporary solution 1 and a temporary residue 1; soaking the temporary residue 1 with ethanol 70% in a ratio of 1:13 w/v, supported ultrasonic waves at a frequency of 0.2-0.3 kHz for 60 minutes to obtain a temporary mixture to obtain a temporary solution 2 and a temporary residue 2; soaking the temporary residue 2 with ethanol 70% in a ratio of 1:7 w/v, supported ultrasonic waves at a frequency of 0.2-0.3 kHz for 30 minutes to obtain a temporary mixture 3, centrifuging the temporary mixture 3 at a speed of 3000-4000 rpm for 30-40 minutes to obtain a temporary solution 3 and a temporary residue 3; mixing the temporary solution 1 with the temporary solution 2, and the temporary solution 3 to obtain a base mixture; incubating the base mixture for 3 hours, and evaporating at 45° C.-50° C. with pressure of 100-150 mbar until the humidity reaches 25%-30% to obtain the mushroom extract ingredient.

According to the embodiment of the present invention, the collagen extract ingredient is prepared by performing steps (d1) to (d5), including:

(d1) collecting by-products from herring in listed Table 3 below, including scales, skin and bones in a mass ratio of 1:4:3; wash, drying and grinding into a powder 1;

(d2) soaking the powder 1 with solution NaOH 0.09 M at 4° C. for 3 hours in a ratio of 1:7 w/v, centrifuging at a speed of 8000 rpm for 20 minutes to obtain a solid 1, and washing the solid 1 with water twice;

(d3) soaking the solid 1 at step (d1) with butyl alcohol solution 13% for 45 minutes in a ratio of 1:15 w/v, centrifuging at a speed of 8000 rpm for 20 minutes to obtain a solid 2, and washing the solid 2 with water twice;

(d4) soaking the solid 2 with $H_2O_2$ solution 5% in a ratio of 1:5 w/v for 10 minutes, centrifuging at a speed of 8000 rpm for 20 minutes to obtain a solid 3, and washing the solid 3 with water twice; and (d5) soaking the solid 3 with a pineapple and papaya juice mixture in a ratio of 1:3 w/v for 1 hours, supported ultrasonic waves at a frequency of 0.2-0.3 kHz for 60 minutes, adding pepsin solution 0.45% mixed in 0.6 M acetic acid at 2.5° C.-3° C. for 24 hours according to 1 part of the solid 3:8 parts of pepsin solution w/v, centrifuging at a speed of 8000 rpm at 4° C. for 20 minutes to obtain a supernatant, adjusting pH to 6.8-7.2 with tris base 0.5 M, then precipitate with 2.5 M NaCl solution, and centrifuging at 8000 rpm at 4° C. for 20 min to form precipitate; dissolving the precipitate in 0.5 M acetic acid, dialyzing in 0.1 M acetic acid and distilling water for 48-72 hours, and freeze-drying to obtain the collagen extract ingredient.

According to the priority embodiment of the invention, the by-products from herring is selected from the one or more in the genus *Sardinella* of the including *Sardinella aurita*, *Sardinella jussieu*, *Sardinella albella*, *Sardinella atricauda*, *Sardinella brachysoma*, *Sardinella fijiense*, *Sardinella fimbriata*, *Sardinella hualiensis*, *Sardinella marquesensis*, and *Sardinella melanura*.

According to the priority embodiment of the invention, the pineapple and papaya juice mixture is prepared by mixing a pineapple juice with a papaya juice in a ratio of (1-5):(1-5) v/v, preferably the ratio of 1:1, 2:1 and 3:1.

It should be noted that the pineapple juice is primarily obtained through a mechanical pressing process where the pulp of ripe pineapples is crushed to extract the juice. This process involves cleaning the pineapples, peeling and extracting the pulp, and then pressing the pulp to separate the liquid. Similar to pineapple juice, papaya juice is obtained through several methods, such as blend papaya chunks with water or juice in a blender, or use a juicer to extract the juice.

According to the embodiment of the present invention, the solution containing 4-allylpyrocatechol is prepared by performing steps (e1) to (e3), including:

(e1) grinding betel leaves with water in a ratio of 1:5 w/v, treating the ground betel leaves by ultrasonically at a frequency of 0.1 kHz for 2 hours, and steam distilled for 2.5 hours to obtain an extract solution 1 and a remaining solution after distillation;

(e2) mixing the remaining solution after distillation with diethyl ester solution in a ratio of 1:(1-5) v/v, evaporating the centrifuged mixture at 45° C.-50° C., pressure of 100-150 mbar until the humidity reaches 25%-30% to obtain a concentrate; purifying the concentrate through silica gel column chromatography with a hexane-ethyl acetate solvent in a ratio of 9:1, then purifying again one more on a C18 column with MeOH:$H_2$O fraction in a ratio of 1:1 to obtain a white solid which is 4-allylpyrocatechol compound; and (e3) dissolving the extract solution 1 at step (e1) with the white solid obtained in step (e2) at temperatures of 30° C.-42° C., with stirring at an average speed of 400 rpm for 15 minutes to obtain the solution containing 4-allylpyrocatechol.

According to the embodiment of the present invention, the plant-derived nanovesicles ingredient is prepared by mixing a first nanovesicles ingredient with a second nanovesicles ingredient in a ratio of 2:3 w/w.

According to the embodiment of the present invention, the first nanovesicles ingredient is prepared by performing steps (f1) to (f8):

(f1) collecting a plant mixture consisting of 2 parts of *Illicium verum* Hook. f., 3 parts of *Artemisia vulgaris*, and 3 parts of *Piper sarmentosum;*

(f2) washing three times with deionized water at 20° C.-25° C.;

(f3) pureeing the washed plant mixture with phosphate buffer solution (PBS) in a ratio of 1:3 w/v at a speed of 7000-8000 rpm for 15 minutes to obtain a first temporary solution;

(f4) filtering the first temporary solution by a filter membrane with a diameter 0.20-0.22 μm to obtain a second temporary solution;

(f5) centrifuging the second temporary solution by ultracentrifugation at 120000×g for 100 min at 4° C. to obtain a temporary solid;

(f6) dissolving the temporary solid in phosphate buffer solution (PBS), transferring to a 45% sucrose gradient solution, and ultracentrifugation at 130000×g for 100 min to obtain a third temporary solution;

(f7) washing the third temporary solution with PBS and centrifuging at 150000×g for 60 min at 4° C. to obtain a fourth temporary solution; and (f8) filtering the fourth temporary solution through a filter membrane with a diameter 0.20-0.22 μm to obtain the first nanovesicles ingredient.

According to the embodiment of the present invention, the second nanovesicles ingredient is prepared by performing steps (g1) to (g9):

(g1) collecting a fruit mixture including 3 parts of dragon fruit (*Hylocereus undatus, Hylocereus costaricensis, Hylocereus megalanthus, Hylocereus undatus costaricensis*), 3 parts of avocado (*Persea americana*), and 1 part of watermelon (*Citrullus lanatus*);

(g2) washing the fruit mixture three times with deionized water at 20° C.-25° C.;

(g3) pureeing the washed fruit mixture with phosphate buffer solution (PBS) in a ratio of 1:1 (g/mL) at a speed of 7000-8000 rpm for 15 minutes to obtain a first foundation solution;

(g4) filtering the first foundation solution by a filter membrane with a diameter 0.20-0.22 μm to obtain a second foundation solution;

(g5) centrifuging the second foundation solution by ultracentrifugation at 100000×g for 60 min to obtain a residue;

(g6) dissolving the residue in phosphate buffer solution (PBS), transferring to a 45% sucrose gradient solution, and ultracentrifugation at 130000×g for 100 min to obtain a third foundation solution;

(g7) stirring the third foundation solution with a 10% polyethylene glycol-8000 (PEG8000) solution in a ratio of 1:1 v/v, and incubating for 8-10 hours at 4° C., then centrifuging at 110000×g for 40 minutes at 4° C. to obtain a precipitate;

(g8) dissolving the precipitate in phosphate buffer solution (PBS) in a ratio of 1:2 w/v to obtain a foundation solution; and (g9) filtering the foundation solution by a tangential flow filtration (TFF) to obtain the second nanovesicles ingredient; wherein the technical specifications related to TFF include a molecular size of 500 kDa, and filtering at a flow rate of 20 mL/min with the transmembrane pressure maintained at 2 bar.

At step 102, mixing homogenizing the solution containing 4-allylpyrocatechol with the plant-derived nanovesicles ingredient prepared in step 101 at temperatures of 30° C.-50° C., with stirring at an average speed of 400 rpm for 15 minutes to obtain a solution 10.

At step 103, mixing homogenizing the herbal concentrate with the herbal powder mixture, the mushroom extract ingredient, the collagen extract ingredient, and the solution 10 at temperatures of 30° C.-50° C., with stirring at an average speed of 400 rpm for 15-45 minutes to obtain a foundation mixture.

Within the scope of the present invention, the term "foundation mixture" includes the following meanings:

(a) A foundation mixture is a solution/or mixture that completely dissolves/mixing homogenizing the herbal concentrate, the herbal powder mixture, the mushroom extract ingredient, the collagen extract ingredient, the solution containing 4-allylpyrocatechol, and the plant-derived nanovesicles ingredient having the correct a predetermined ratio;

(b) A homogeneous mixture is act as a reactant, allowing the addition of ingredients to contribute their chemical and physical properties to create a new preparation; and (c) A homogeneous mixture chemically bonds with other complementary ingredients including but not limited such as ionization reactions, covalent reactions, reducing reactions, replacement reactions, and rearrangement reactions to form a new chemical composition.

According to the embodiment of the present invention, at step 103, said first predetermined percentage (%) by weight is between 25% to 60%, said second predetermined percentage (%) by weight is between 20% to 60%, said third predetermined percentage (%) by weight is between 0.5% to 18%, said fourth predetermined percentage (%) by weight is between 0.1% to 20%, said fifth predetermined percentage (%) by weight is between 0.01% to 0.45%, and said sixth predetermined percentage (%) by weight is between 0.02% to 0.2% of the total weight of said foundation mixture.

According to the preferred embodiment of the present invention, at step 103, said first predetermined percentage (%) by weight is between 30% to 60%, said second predetermined percentage (%) by weight is between 30% to 60%, said third predetermined percentage (%) by weight is between 1.5% to 18%, said fourth predetermined percentage (%) by weight is between 2.5% to 20%, and said fifth predetermined percentage (%) by weight is between 0.01% to 0.45%, and said sixth predetermined percentage (%) by weight is between 0.02% to 0.2% of the total weight of said foundation mixture.

At step 104, creating a base solution, wherein 100 ml of the base solution created by mixing performed in a specific order from (h1) to (h3) comprising:

(h1) adding 125 mg of the foundation mixture with 100 mg of glycyrrhizic acid, 50 mg of a phospholipid component, and 315 mg of lipoid S100 into a reaction tank, adding 0.2 part of absolute ethanol, refluxing at 60° C. for 2 hours to obtain a solution 20;

(h2) dissolving 250 mg of chitosan with 10 mL of distilled water, slowly adding 0.5 mL of glacial acetic acid, combined with stirring 50 rpm, adding 30 mL of water and let stand until the solution is clear, transferring the cleared solution into a 50 mL volumetric flask, and adding distilled water to the mark to obtain 50 mL of a chitosan solution with concentration of 5 mg/mL; and (h3) dissolving 1 mL of the chitosan solution at step (f2) with 300 mg of a poloxamer component and 85 mL of distilled water, cooling the reaction mixture and stirring at 600 rpm until the reaction mixture is homogeneous, injecting 8 mL of the solution 10 at a rate of 1 mL/min with a stirring speed of 1000 rpm for 30 minutes, and adding distilled water to make 100 mL of the base solution.

According to the preferred embodiment of the present invention, the poloxamer component is selected from the group consisting of poloxamer 124, poloxamer 188, poloxamer 237, poloxamer 338, and poloxamer 407.

According to the preferred embodiment of the present invention, the phospholipid component is selected from the group consisting of phosphatidylcholine (DMPC), phosphatidylserine (PS), and phosphatidylethanolamine (PE).

At step 105, mixing the base solution with an excipient ingredient in a ratio of 1:(12-30) w/w, and evaporating the centrifuged mixture at 45° C.-50° C., pressure of 100-150 mbar until the humidity reaches 10%-20% to obtain the herbal oral composition having the properties for supporting and enhancing musculoskeletal health.

According to the invention, the excipient ingredient is prepared by mixing corn starch, lactose, talc, nipagin, propylparaben and magnesium stearate in the ratio of 3.5:1.5:2.5:1:1:1.5 by mass.

Finally, at step 106, shaping and packaging the herbal oral composition having the properties for supporting and enhancing musculoskeletal health.

According to the embodiment of the present invention, a herbal oral composition having the properties for supporting and enhancing musculoskeletal health 200 ("composition 200") including: a herbal concentrate having 25% to 60% by weight, a herbal powder mixture having 20% to 60% by weight, a mushroom extract ingredient having 0.5% to 18% by weight, a collagen extract ingredient having 0.1% to 20% by weight, a solution containing 4-allylpyrocatechol having 0.01% to 0.45% by weight, and a plant-derived nanovesicles ingredient having 0.02% to 0.2% by weight; wherein the composition 200 is produced by the process 100 comprising steps 101 to 106 described in detail above.

According to the preferred embodiment of the present invention, the composition 200 including: the herbal concentrate having 30% to 60% by weight, the herbal powder mixture having 30% to 60% by weight, the mushroom extract ingredient having 1.5% to 18% by weight, the collagen extract ingredient having 2.5% to 20% by weight, the solution containing 4-allylpyrocatechol having 0.01% to 0.45% by weight, and the plant-derived nanovesicles ingredient having 0.02% to 0.2% by weight.

According to other embodiments of the invention, the form of the composition 200 is produced by the process 100 of the present invention may be capsules, tablets, or hard gelatin capsules, depending on the dosage form thereof.

Besides capsules, the composition 200 may be provided as a tablet, aqueous or oil suspension, dispersible powder or granule, emulsion, hard or soft capsule, syrup, elixir, or beverage. The composition 200 intended for oral use may be prepared according to any method known in the art for the manufacture of pharmaceutically acceptable compositions and such compositions may contain one or more of the following agents: sweeteners, flavoring agents, coloring agents and preservatives. The sweetening and flavoring agents will increase the palatability of the preparation. Tablets containing extracts in admixture with non-toxic pharmaceutically acceptable excipients suitable for tablet manufacture are acceptable. Pharmaceutically acceptable means that the agent should be acceptable in the sense of being compatible with the other ingredients of the formulation (as well as non-injurious to the patient). Such excipients include inert diluents such as calcium carbonate, sodium carbonate, lactose, calcium phosphate or sodium phosphate; granulating and disintegrating agents, such as corn starch or alginic acid; binding agents such as starch, gelatin or acacia; and lubricating agents such as magnesium stearate, stearic acid or talc. Tablets can be uncoated or can be coated by known techniques to delay disintegration and absorption in the gastrointestinal tract and thereby provide a sustained action over a longer period of time. For example, a time delay material such as glyceryl monostearate or glyceryl distearate alone or with a wax may be employed.

The composition 200 for oral use can also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil. In some embodiments, aqueous suspensions can contain an extract of the invention in admixture with excipients suitable for the manufacture of aqueous suspensions. Such excipients include, but are not limited to, suspending agents, dispersing or wetting agents, one or more preservatives, one or more coloring agents, one or more flavoring agents and one or more sweetening agents such as sucrose or saccharin. Oil suspensions may be formulated by suspending the active ingredient in a vegetable oil, such as arachis oil, olive oil, sesame oil or coconut oil, or in a mineral oil such as liquid paraffin. The oil suspension may contain a thickening agent, such as beeswax, hard paraffin or cetyl alcohol. Sweetening agents, such as those set forth above, and flavoring agents may be added to provide a palatable oral preparation. These formulations may be preserved by an added antioxidant such as ascorbic acid. Dispersible powders and granules of the invention suitable for preparation of an aqueous suspension by the addition of water provide one or more extracts in admixture with a dispersing or wetting agent, a suspending agent, and one or more preservatives. Additional excipients, for example sweetening, flavoring and coloring agents, may also be present.

It is important to understand that all weights referring to herbs in the above description are the dry weights of those herbs. While dried material is traditionally used and preferred, it must be recognized that drying of plant materials facilitates their storage, transportation and subsequent processing. Drying may not be a requirement to derive the benefits of these herbs. As such, the present invention may be practiced with the listed fresh plant materials as well. The use of fresh plant materials, sufficient to meet the requisite quantity and proportions of the extracts used, come under the scope of the present invention.

It is understood that several species within a plant genus may be given under a particular plant's entry in the Pharmacopoeia and these species with the same genus may be freely substituted by, or used in conjunction with, other members of the same genus as given in the Pharmacopoeia.

In addition, it is recognized that certain plant parts may contain the active components of interest in higher concentration and the present invention teaches the use of specific plant parts under the standardized nomenclature of the Pharmacopoeia. However, these components may also be present in the other parts of the same plants. As such, the components of interest may also be extracted from other parts of the same plant under the scope of the present claims.

A person skilled in the art will appreciate that it is possible, with plant cell and tissue culture techniques, to culture the cells and tissue of these herbs in vitro and to extract the active components of interest from these cells and tissue.

The extraction process entailed reducing the size of the herbal materials. Here, the reducing in size may be achieved by a number of ways including, but not limited to, cutting, chopping, mincing, pounding, pulverizing, milling and grinding. While one way may be taught, other ways and means of achieving a reduction in size of the materials may also be used.

TABLE 1

| Mixing ingredients of the composition 200 is produced by the method 100 according to the invention | | | |
|---|---|---|---|
| No. | Name of | Percentage (%) | Optimal percentage (%) |
| 1 | The herbal concentrate | 25-60 | 30-60 |
| 2 | The herbal powder mixture | 20-60 | 30-60 |
| 3 | The mushroom extract ingredient | 0.5-18 | 1.5-18 |
| 4 | The collagen extract ingredient | 0.1-20 | 2.5-20 |
| 5 | The solution containing 4-allylpyrocatechol | 0.01-0.45 | 0.01-0.45 |
| 6 | The plant-derived nanovesicles ingredient | 0.02-2 | 0.02-2 |

TABLE 2

| List of 19 types of medicine herbals in Vietnam according to the invention | | | | | |
|---|---|---|---|---|---|
| Symbol | Scientific name of the herb | Part used | Active ingredients | Uses | Distribution |
| (A) | Angelica pubescens | Tuberous root | Coumarins, furanocoumarins, ferulic acid, essential oil(s) | Treats joint pain due to rheumatism, rhinitis, runny nose, toothache | Northern Vietnam |
| (B) | Cinnamomum cassia | Branchlet | Cinnamaldehyde, cinnamyl acetate, eugenol, coumarin | Treats common cold, abdominal pain, joint pain | Vietnam |
| (C) | Asarum heterotropoides | Root | Aristolochic acid, methyl eugenol, safrole, asarone, pinene | Treats cough and asthma, headache, toothache, rheumatic pain | Northern Vietnam |
| (D) | Ligusticum wallichii | Rhizome | Ligustilide, tetramethylpyrazine (TMP), ferulic acid, essential oil(s) | Promotes blood circulation, relieves pain; treats headache, menstrual pain, pain due to blood stasis, rheumatism | Northern Vietnam |
| (E) | Angelica sinensis | Root | Ligustilide, ferulic acid, polysaccharides, vitamin B12 | Treats anemia, irregular menstruation, menstrual pain | Northern Vietnam |
| (F) | Saposhnikovia divaricata | Root | Chromones (prim-O-glucosylcimifugin, cimifugin), coumarins, polysaccharides | Treats common cold, headache, rheumatic joint pain, itchy skin | Northern Vietnam |
| (G) | Eucommia ulmoides | Stem bark | Lignans (pinoresinol diglucoside), iridoids (geniposidic acid), aucubin, gutta- | Strengthens tendons and bones, calms the fetus; treats lower back and knee pain, weak | Northern Vietnam |

TABLE 2-continued

List of 19 types of medicine herbals in Vietnam according to the
invention

| Symbol | Scientific name of the herb | Part used | Active ingredients | Uses | Distribution |
|---|---|---|---|---|---|
| | | | percha, polysaccharides | tendons and bones, high blood pressure, threatened miscarriage | |
| (H) | Achyranthes bidentata | Tuberous root | Triterpenoid saponins (achyranthine), ecdysterone, polysaccharides, potassium | Treats back pain, joint pain, irregular menstruation, difficult urination | Northern Vietnam |
| (I) | Poria cocos | Sclerotium | Polysaccharides (pachyman), triterpenes (pachymic acid), ergosterol | Treats edema, scanty urination, diarrhea, poor appetite due to spleen deficiency, palpitations, insomnia | Ha Giang, Thanh Hoa, Lam Dong, Gia Lai (Vietnam) |
| (K) | Glycyrrhiza uralensis | Root | Glycyrrhizin (glycyrrhizic acid), liquiritin, glabridin, flavonoids, polysaccharides | Relieves pain, treats cough, abdominal pain, detoxifies | Northern Vietnam |
| (L) | Loranthus parasiticus | Branchlet | Flavonoids (quercetin, hyperin, avicularin), triterpenes, lectins | Treats lower back and knee pain, numbness/ rheumatism, threatened miscarriage, high blood pressure | Northern and Central Vietnam |
| (M) | Paeonia lactiflora | Tuberous root | Paeoniflorin, albiflorin, benzoic acid, tannins, monoterpenoid glycosides | Treats blood deficiency, irregular menstruation, abdominal pain, headache, convulsions | Northern Vietnam |
| (N) | Rehmannia glutinosa | Tuberous root | Iridoid glycosides (catalpol, rehmanniosides), stachyose, mannitol, polysaccharides | Treats high fever, bleeding, thirst; anemia, lower back and knee pain | Northern Vietnam |
| (O) | Justicia gendarussa | Root | Alkaloids (justicin, gendarusin A, B), flavonoids, lignans, triterpenes | Treats aching joints and bones, traumatic hematoma (bruising with blood stagnation), menstrual pain | Northern Vietnam |
| (P) | Tinospora sinensis | Stem | Alkaloids (berberine, palmatine, jatrorrhizine), diterpenoid lactones (tinosporide), polysaccharides, tinosporan | Clears heat, detoxifies, promotes diuresis to remove dampness, anti-inflammatory; Treats fever, sore throat, boils, rheumatism, dysentery | Vietnam |
| (Q) | Chrysanthemum indicum | Flower | Flavonoids (luteolin, apigenin, acacetin), essential oil(s) (borneol, camphor, chrysanthenone), chlorogenic acid | Dispels wind-heat, clears heat, detoxifies, improves vision; treats wind-heat common cold, headache, dizziness, red, | Northern Vietnam |

TABLE 2-continued

List of 19 types of medicine herbals in Vietnam according to the invention

| Symbol | Scientific name of the herb | Part used | Active ingredients | Uses | Distribution |
|---|---|---|---|---|---|
| (R) | Brassica alba | Seed | Myrosin, sinapine, sinalbin, sinigrin, fatty oils, saponins | swollen and painful eyes, boils Anti-inflammatory, reduces swelling, treats musculoskeletal pain | Vietnam |
| (T) | Vitex negundo | Leaf | Flavonoids (casticin, vitexin, isovitexin), iridoid glycosides (agnuside, aucubin), alkaloids, essential oil(s) | Dispels wind, eliminates dampness, reduces inflammation, relieves pain; treats common cold, headache, bronchitis, asthma, rheumatic joint pain, neuralgia | Vietnam |
| (U) | Justicia gendarussa | Stem bark | Alkaloids (justicin, gendarusin A, B), flavonoids, lignans, triterpenes | Similar to root: Promotes blood circulation, dispels wind, eliminates dampness, relieves pain, reduces swelling | Northern Vietnam |

TABLE 3

List of 10 herring species in Vietnam according to the invention

| No. | Scientific name | Characteristics | Distribution |
|---|---|---|---|
| 1 | Sardinella aurita | Body is rounder, less scaly; dark flesh, less fat, less bone | Coastal waters of Vietnam, from Quang Nam to Nghe An, and coastal waters of Northern Vietnam |
| 2 | Sardinella jussieu | Body is slender, many whitish-green shiny scales; flesh is white, fragrant, fatty, and firm, but with many small bones | Coastal waters of Vietnam, from Northern Vietnam to central provinces like Thanh Hoa, Ha Tinh, Quang Binh, and coastal waters of Binh Thuan, Saigon River basin, and Co Chien River (Ben Tre) |
| 3 | Sardinella albella | Body is slender, easily loses scales | Coastal waters of Vietnam |
| 4 | Sardinella atricauda | Body is elongated, slender; easily loses scales, body has an iridescent silvery color | Coastal waters of Vietnam |
| 5 | Sardinella brachysoma | Body height is greater than body length | Coastal waters of Vietnam |
| 6 | Sardinella fijiense | Body is elongated, somewhat cylindrical, slender, large scales, easily loses scales, blue-green iridescent back, shiny silver belly | Coastal waters of Vietnam |
| 7 | Sardinella fimbriata | Has serrated scales | Ba Ria-Vung Tau |
| 8 | Sardinella hualiensis | Long body, slender, serrated abdominal fins, iridescent blue-green back | Coastal waters of Vietnam |
| 9 | Sardinella marquesensis | Long body, slender, blue back, white belly, no dark spots | Coastal waters of Vietnam |
| 10 | Sardinella melanura | Dark caudal fin | Van Phong Bay (Khanh Hoa) |

EXAMPLES

The following experimental section is provided purely by way of illustration and is not intended to limit the scope of the invention as defined in the appended claims. In the following experimental section, reference is made to the appended drawings, wherein:

Example 1: Production of Composition 200 According to Method 100

Method 100 is applied to produce composition 200 from 100 kg of input raw materials, using three formulations: 1, 2, and 3, as illustrative examples. The components and the weight of each input material in each formulation are presented in Table 4 below.

TABLE 4

Components and weights of the materials for composition 200
corresponding to formulations 1, 2, and 3

| Component | Formulation 1 (kg) | Formulation 2 (kg) | Formulation 3 (kg) |
|---|---|---|---|
| The herbal concentrate | 59.85 | 47.7 | 42.55 |
| The herbal powder mixture | 30 | 35 | 32 |
| The mushroom extract ingredient | 5 | 7 | 10 |
| The collagen extract ingredient | 5 | 10 | 15 |
| The solution containing 4-allylpyrocatechol | 0.1 | 0.2 | 0.3 |
| The plant-derived nanovesicles ingredient | 0.05 | 0.1 | 0.15 |

Wherein, the herbal concentrate is prepared using method 100 from 26.9 kg of input raw materials, provided as an illustrative example. The components and the weight of the input materials in this illustrative example are listed in Table 5.

TABLE 5

Components and weights of the input materials used for the
preparation of the herbal concentrate.

| No. | Medicine herbal | Weight (kg) |
|---|---|---|
| 1 | Angelica pubescens | 2.25 |
| 2 | Cinnamomum cassia | 1.5 |
| 3 | Asarum heterotropoides | 1.5 |
| 4 | Ligusticum wallichii | 1.5 |
| 5 | Angelica sinensis | 1.5 |
| 6 | Saposhnikovia divaricata | 2 |
| 7 | Eucommia ulmoides | 1.5 |
| 8 | Achyranthes bidentata | 2.25 |
| 9 | Poria cocos | 1.5 |
| 10 | Glycyrrhiza uralensis | 1.5 |
| 11 | Loranthus parasiticus | 1.5 |
| 12 | Paeonia lactiflora | 1.5 |
| 13 | Rehmannia glutinosa | 1.5 |
| 14 | Justicia gendarussa | 1.5 |
| 15 | Tinospora sinensis | 1.2 |
| 16 | Chrysanthemum indicum | 1.2 |
| 17 | Brassica alba | 0.5 |
| 18 | Vitex negundo | 0.5 |
| 19 | Justicia gendarussa | 0.5 |

Wherein, the herbal powder mixture is prepared using method 100 from 25.9 kg of input raw materials, provided as an illustrative example. The components and the weight of the input materials in this illustrative example are listed in Table 6.

TABLE 6

Components and weights of the input materials used for the
preparation of the herbal powder mixture

| No. | Medicine herbal | Weight (kg) |
|---|---|---|
| 1 | Angelica pubescens | 2.25 |
| 2 | Cinnamomum cassia | 1.5 |
| 3 | Asarum heterotropoides | 1.5 |
| 4 | Ligusticum wallichii | 1.5 |
| 5 | Angelica sinensis | 1.5 |
| 6 | Saposhnikovia divaricata | 2 |
| 7 | Eucommia ulmoides | 1.5 |
| 8 | Achyranthes bidentata | 2.25 |
| 9 | Poria cocos | 1.5 |
| 10 | Glycyrrhiza uralensis | 1.5 |
| 11 | Loranthus parasiticus | 1.5 |
| 12 | Paeonia lactiflora | 1.5 |
| 13 | Rehmannia glutinosa | 1.5 |
| 14 | Justicia gendarussa | 1.5 |
| 15 | Tinospora sinensis | 1.2 |
| 16 | Chrysanthemum indicum | 1.2 |
| 17 | Brassica alba | 0.5 |

Wherein, the mushroom extract ingredient is prepared using method 100 from 10 kg of input raw materials, provided as an illustrative example. The components and the weight of the input materials in this illustrative example are listed in Table 7.

TABLE 7

Components and weights of the input materials used for the
preparation of the mushroom extract ingredient

| No. | Mushroom | Weight (kg) |
|---|---|---|
| 1 | Auricularia auricula | 2.5 |
| 2 | Tremella fuciformis | 2.5 |
| 3 | Lentinus edodes | 2.5 |
| 4 | Hericium erinaceus | 2.5 |

Example 2: Acute Oral Toxicity Test Design for Composition 200

(I) Materials and experimental animals: Female Swiss albino mice, aged 6-7 weeks and weighing between 25 and 30 grams, were used as the animal model in this study. All animals were acclimated for 7 days prior to the start of the experiment to ensure physiological stability. Mice were housed in glass cages, with five animals per cage, and bedding was provided using sterilized wood chips. Environmental conditions were maintained at an ambient temperature of 22±2° C., relative humidity of 50%-60%, and a 12-hour light/dark cycle. Animals were fed a standard pellet diet and given reverse-osmosis (RO) water ad libitum throughout the experiment. The test substance, Composition 200 according to formulation 2 of example 1, was prepared by dissolving or suspending it in 0.9% normal saline to achieve the required concentrations for oral administration by gavage.

(II) Group Allocation and Dosing

A total of 24 mice were randomly divided into 4 groups (6 mice/group):
Control group: Received 0.9% saline at 5 mL/kg body weight;
Group CP100-1000: Single oral dose of 1000 mg/kg composition 200;

Group CP100-3000: Single oral dose of 3000 mg/kg composition 200;

Group CP100-5000: Single oral dose of 5000 mg/kg composition 200.

(III) Dosing and observation procedures: On Day 0 (pre-dosing), the body weight of each mouse was recorded, and the animals were randomly assigned into treatment groups to ensure unbiased distribution. For dosing, mice were fasted for 4 hours prior to administration. The test substance was administered via oral gavage, with the total volume not exceeding 10 mL/kg of body weight to avoid discomfort or aspiration. Short-term observations were conducted intensively on Day 0. Each animal was observed continuously for 30 minutes immediately following administration and then monitored at 1, 2, 4, and 8 hours post-dose. Observational parameters included changes in skin, fur, eyes, and mucous membranes, as well as respiration, locomotor activity, salivation, diarrhea, convulsions, and tremors. Long-term observations were carried out once daily from Day 1 through Day 14. Animals were evaluated for general activity levels, behavior, food and water intake, and excretory patterns. Body weights were again recorded on Days 7 and 14 to assess any treatment-related effects on growth or general health.

(IV) Evaluation Criteria

Mortality: Number and timing of deaths;

Clinical signs: Any abnormal physical or behavioral symptoms;

Body weight: Tracked changes over time using:

$$\% \Delta BW = \frac{BW Day x - BW Day 0}{BW Day 0} 100\%$$

$LD_{50}$ estimation: Based on observed deaths per OECD 425[1];

Toxicity classification (GHS):

$LD_{50} > 5000$ mg/kg: Category 5: Not classified as acutely toxic via oral route;

$LD_{50}$ between 2000-5000 mg/kg: Category 4;

$LD_{50}$ between 300-2000 mg/kg: Category 3.

(V) Results

TABLE 8

| | | | | | Acute oral toxicity parameters of composition 200 in Swiss albino mice | | | | |
|---|---|---|---|---|---|---|---|---|---|
| Group | Dose (mg/ kg) | n (mice) | Mor-tality (n/ %) | Severe clinical signs (n) | Avg BW Day 0 (g) | Avg BW Day 7 (g) | Avg BW Day 14 (g) | % BW Change (Day 14) | |
| Control | 0 | 6 | 0 (0%) | 0 | 28.0 ± 1.2 | 29.5 ± 1.1 | 30.2 ± 1.3 | +7.9 ± 0.9% | |
| CP100-1000 | 1000 | 6 | 0 (0%) | 0 | 27.8 ± 1.3 | 29.1 ± 1.0 | 29.9 ± 1.4 | +7.6 ± 1.1% | |
| CP100-3000 | 3000 | 6 | 0 (0%) | 0 | 28.2 ± 1.1 | 29.8 ± 1.2 | 30.5 ± 1.0 | +8.2 ± 1.0% | |
| CP100-5000 | 5000 | 6 | 0 (0%) | 0 | 28.1 ± 1.0 | 29.6 ± 1.3 | 30.3 ± 1.1 | +7.8 ± 1.2% | |

Based on Table 8, none of the mice in the CP100-1000, CP100-3000, or CP100-5000 groups experienced mortality (0/6), matching the control group, which indicates an estimated $LD_{50}$ exceeding 5000 mg/kg. No severe clinical signs, such as convulsions, tremors, respiratory distress, diarrhea, or excessive salivation, were observed during the 14-day monitoring period. Regarding body weight changes, the control group exhibited a mean increase of +7.9%±0.9% by Day 14, while the CP100-1000, CP100-3000, and CP100-5000 groups showed mean increases of +7.6%±1.1%, +8.2%±1.0%, and +7.8%±1.2%, respectively, with no statistically significant differences compared to control (p>0.05). These findings demonstrate that Composition 200 does not impair growth or metabolic function in mice at doses up to 5000 mg/kg. Therefore, based on mortality, clinical observations, and comparable weight gain, composition 200 is considered acutely safe via oral administration and meets the criteria for GHS Category 5 (no acute oral toxicity classification).

Example 3: Assessment of the Therapeutic Support Effect of Composition 200 in Freund's Complete Adjuvant-Induced Rheumatoid Arthritis in Mice (I) Materials and methods: Female Swiss-albino mice, aged 6-8 weeks and weighing 25-30 g, were used in the study. The animals were housed under standard conditions with a temperature of 22±2° C., relative humidity of 50-60%, and a 12-hour light/dark cycle. They were provided with standard pellet feed and reverse-osmosis water ad libitum. All animals were acclimated for 7 days prior to the experiment. Freund's Complete Adjuvant (FCA) obtained from Sigma-Aldrich was used to induce arthritis. Composition 200 according to formulation 2 of example 1, the test item, was prepared as a suspension or solution in 0.9% saline and administered via oral gavage. Mobic® (meloxicam) at a dose of 1 mg/kg/day was used as the positive control. A total of 36 mice were randomly divided into six groups (n=6 per group) for treatment allocation.

TABLE 9

| Experimental group allocation and treatment regimens | |
|---|---|
| Group | Treatment |
| Negative Control (NC) | No FCA (no arthritis); oral 0.9% saline |
| Disease Control (DC) | FCA only; oral 0.9% saline |
| Mobic ® Control | FCA + Meloxicam 1 mg/kg/day |
| CP100-Low | FCA + Composition 200, 200 mg/kg/day |
| CP100-Medium | FCA + Composition 200, 300 mg/kg/day |
| CP100-High | FCA + Composition 200, 400 mg/kg/day | in which:

FCA induction (Day 0): 0.1 mL FCA injected into the left hind paw of every mouse except NC;

Treatment period (Days 1-28): Daily oral gavage of the assigned test item or saline;

Study duration: 28 days total.

(II) Endpoints and Measurements (A) Clinical observations (Days 0, 7, 14, 21, and 28): Throughout the study, clinical parameters were monitored at regular intervals to assess disease progression and the effects of treatment. Body weight (in grams) was recorded on Days 0, 7, 14, 21, and 28 to evaluate general health and systemic impact. The diameter of the left ankle joint was measured using a digital vernier caliper at the tibiotarsal region to quantify joint swelling. Hind-paw volume was assessed using a water plethysmometer, providing a precise measurement of inflammation-related edema. Hind-paw surface temperature was measured with a non-contact infrared thermometer to monitor localized inflammation. Arthritis severity was scored using a semi-quantitative scale from 0 to 4 based on visible signs of inflammation and paw deformity:

0=no swelling;

1=mild swelling;

2=moderate swelling;

3=marked swelling with redness;

4=severe swelling with joint deformity.

(B) Hematology and serum biochemistry (Day 28): At the end of the treatment period (Day 28), blood samples were collected to evaluate systemic inflammatory responses. Total leukocyte count (WBC) was determined and expressed as $\times 10^3$ cells/mm$^3$. Differential leukocyte counts were also performed to measure lymphocytes, monocytes, and granulocytes. Inflammatory biomarkers including C-reactive protein (CRP, mg/L) and Rheumatoid Factor (RF, mg/L) were quantified in serum to assess the systemic inflammatory status associated with rheumatoid arthritis.

(C) Histopathology of the ankle joint (Day 28): On Day 28, animals were euthanized, and the left ankle joints were dissected for histological evaluation. The joints were fixed in 10% neutral buffered formalin, decalcified, embedded in paraffin, sectioned, and stained using hematoxylin and eosin (H&E). Microscopic evaluation focused on identifying pathological changes such as synovial membrane inflammation, pannus formation, cartilage erosion, and subchondral bone damage, which are hallmarks of arthritis progression.

(III) Results

TABLE 10

| | Joint diameter (cm) | Paw volume (cm$^3$) | Paw temperature (° C.) | Arthritis score (0-4) | CRP (mg/L) | RF (mg/L) | WBC ($\times 10^3$/ mm$^3$) |
|---|---|---|---|---|---|---|---|
| Group | | | | | | | |
| NC (no FCA) | 1.20 ± 0.05 | 0.25 ± 0.02 | 30.0 ± 0.2 | 0 ± 0 | 0.10 ± 0.02 | 0.50 ± 0.10 | 4.0 ± 0.3 |
| DC (FCA only) | 4.20 ± 0.10 | 1.00 ± 0.05 | 33.0 ± 0.3 | 4 ± 0 | 2.50 ± 0.20 | 4.00 ± 0.30 | 9.5 ± 0.5 |
| Mobic ® (1 mg/kg) | 1.50 ± 0.07 | 0.30 ± 0.03 | 30.2 ± 0.2 | 1 ± 0 | 0.50 ± 0.05 | 1.60 ± 0.20 | 4.5 ± 0.4 |
| CP100-L (200 mg/kg) | 3.50 ± 0.10 | 0.75 ± 0.04 | 31.5 ± 0.3 | 3 ± 0 | 1.80 ± 0.15 | 3.50 ± 0.25 | 7.0 ± 0.5 |
| CP100-M (300 mg/kg) | 2.50 ± 0.08 | 0.45 ± 0.03 | 30.5 ± 0.2 | 2 ± 0 | 1.20 ± 0.10 | 2.40 ± 0.20 | 5.5 ± 0.4 |
| CP100-H (400 mg/kg) | 1.60 ± 0.05 | 0.32 ± 0.02 | 30.1 ± 0.2 | 1 ± 0 | 0.55 ± 0.05 | 1.70 ± 0.15 | 4.6 ± 0.3 |

Results at day 28 across all experimental groups

Based on Table 10, the Disease Control group exhibited severe arthritis with a joint diameter of 4.20 cm, paw volume of 1.00 cm$^3$, and paw temperature of 33.0° C. In contrast, the Mobic® and CP100-High groups showed near-normal values, with joint diameters of 1.50 cm and 1.60 cm, paw volumes of 0.30 cm$^3$ and 0.32 cm$^3$, and paw temperatures of 30.2° C. and 30.1° C., respectively. The arthritis severity score was 4 in the Disease Control group but dropped to 1 in both Mobic® and CP100-High, indicating minimal residual inflammation. Inflammatory biomarkers followed a similar trend: CRP levels declined from 2.50 mg/L in the Disease Control group to 0.50 mg/L with Mobic® and 0.55 mg/L with CP100-High, while RF decreased from 4.00 mg/L to 1.60 mg/L and 1.70 mg/L, respectively. Total WBC count, elevated at 9.5×10$^3$/mm$^3$ in Disease Control, normalized to 4.5×10$^3$/mm$^3$ with Mobic® and 4.6×10$^3$/mm$^3$ with CP100-High. These results demonstrate that composition 200 at 400 mg/kg provides a level of therapeutic support comparable to Mobic®, effectively ameliorating clinical signs of arthritis, reducing systemic inflammation, and restoring leukocyte counts.

Example 4: Experiment Demonstrating the Efficacy of Composition 200 in Treating Joint Disease Based on the Monosodium Iodoacetate (MIA)-Induced Osteoarthritis Model

(I) Materials and Methods (A) Animals, Reagents, and Test Substances:

Experimental animals: Fifty male Wistar rats (180+20 g, 9-10 weeks old). Rats were housed in groups of five per glass cage with sterilized wood-chip bedding at 22±2° C., 50%-60% relative humidity, under a 12 h/12 h light-dark cycle. Standard pellet diet and reverse-osmosis water were available ad libitum. A 7-day acclimation period preceded all procedures;

OA induction agent: Monosodium iodoacetate (MIA; Sigma-Aldrich), prepared as 10 mg/mL in sterile 0.9% saline;

Composition 200 (according to formulation 2 of example 1): Standardized herbal preparation, vacuum-dried to ~25%-30% moisture. Dosing solutions were made by dissolving/suspending in 0.9% NaCl at concentrations to deliver 200 mg/kg, 300 mg/kg, or 400 mg/kg per day by oral gavage (volume≤10 mL/kg);

Positive control: Indomethacin (25 mg tablets), dissolved in 0.9% NaCl to administer 2 mg/kg/day by oral gavage;

Negative control: Sterile 0.9% NaCl (vehicle).

(B) Group Allocation and Treatment:

Fifty Rats were Randomized (n=10 Per Group) into Five Groups:

Group 1 (Control): No MIA injection; received 0.9% NaCl;

Group 2 (OA Model): MIA injection; received 0.9% NaCl;

Group 3 (Composition 200 Low): MIA injection; received Composition 200 at 200 mg/kg/day;

Group 4 (Composition 200 Mid): MIA injection; received Composition 200 at 300 mg/kg/day;

Group 5 (Composition 200 High): MIA injection; received Composition 200 at 400 mg/kg/day;

Group 6 (Indomethacin): MIA injection; received indomethacin at 2 mg/kg/day.

(C) Osteoarthritis Induction and Treatment Timeline:

Day 0 (Baseline): Body weight recorded for all rats; randomized into groups;

OA induction (Day 0): Under light isoflurane anesthesia, Groups 2-6 received a single intra-articular injection of 50 μL of 10 mg/mL MIA (0.5 mg MIA) into the right knee joint.

Group 1 received 50 μL of sterile 0.9% NaCl instead;

Day 7 (Pre-treatment assessment): Body weight and hind-limb weight-bearing measured to confirm OA induction;

Treatment Phase (Days 8-63, Weeks 2-9):

Groups 3-5 received composition 200 by oral gavage once daily at 200 mg/kg (Group 3), 300 mg/kg (Group 4), or 400 mg/kg (Group 5);

Group 6 received indomethacin 2 mg/kg once daily by oral gavage;

Groups 1-2 received equal volumes of 0.9% NaCl;

All rats were fasted for 4 h prior to each dosing; gavage volume did not exceed 10 mL/kg.

(III) Endpoints and Measurements (A) Weight-Bearing Capacity (Days 0, 7, 21, 35, 49, 63):

Apparatus: Incapacitance tester (IITC Life Sciences);

Procedure: Each rat was placed in a custom holder so that its hind paws rested separately on two force-sensing plates. The mean weight borne by the right (MIA-injected) hind limb (WR) and left (WL) hind limb was recorded over 5 s (average of three consecutive readings);

Calculation:

$$\text{Weight} - \text{bearing ratio (\%)} = \frac{WR}{WL + WR} \times 100\%$$

Time Points:

Day 0 (pre-MIA): Baseline measurement;

Day 7 (pre-treatment): Confirm OA induction;

Day 21:2 weeks of treatment;

Day 35:4 weeks of treatment;

Day 49:6 weeks of treatment;

Day 63:8 weeks of treatment.

(B) Histopathological Evaluation of Knee Joint (Day 63):

Sample collection: At the end of Day 63, rats were anesthetized with pentobarbital sodium (50 mg/kg) and euthanized. Both knee joints were harvested, fixed in 10% neutral buffered formalin for >72 hours, then decalcified in 10% EDTA (pH 7.4) for 14 days;

Sectioning and staining: Paraffin-embedded sagittal sections (5 μm) were stained with hematoxylin & eosin (H&E);

Scoring[2]:

Grade (0-6): Cartilage degeneration severity (0=intact; 6=full-thickness loss);

Stage (0-4): Extent of cartilage surface involvement (0=none; 4=>50%).

Histological score=Grade×Stage (range 0-24);

For each rat, six zones per knee were scored and averaged.

(C) Hematology and Serum Biochemistry (Days 7 and 63):

Blood collection: Tail-vein samples were taken on Day 7 (pre-treatment) and Day 63 (post-treatment). Blood was collected into $K_2$EDTA tubes for hematology and plain tubes for serum;

Hematology: Total leukocyte count (WBC), lymphocyte (LYM), monocyte (MON), and granulocyte (GRA) counts were measured by an automated analyzer (Mindray BC-2800Vet);

Serum assays: After centrifugation (3000 rpm×10 min), serum levels of C-reactive protein (CRP) and rheumatoid factor (RF) were quantified via ELISA kits (Sigma-Aldrich). Optical density was read at 450 nm.

(IV) Results (A) Weight-Bearing Capacity:

TABLE 11

Weight-bearing ratio (%) of the right (MIA-injected) hind limb
(mean ± SD; n = 10)

| Group | Day 0 | Day 7 | Day 21 | Day 35 | Day 49 | Day 63 |
|---|---|---|---|---|---|---|
| 1 (Control (no MIA)) | 51.0 ± 2.3 | 50.7 ± 2.9 | 51.2 ± 2.6 | 50.9 ± 2.7 | 50.8 ± 3.1 | 50.6 ± 2.8 |
| 2 (OA Model (MIA + vehicle)) | 50.8 ± 2.6 | 29.5 ± 3.2 | 30.8 ± 3.4 | 31.7 ± 3.5 | 36.1 ± 3.6 | 37.5 ± 3.9 |
| 3 (Composition 200 (200 mg/kg)) | 50.9 ± 3.1 | 29.3 ± 4.1 | 36.5 ± 3.5 | 40.2 ± 3.8 | 41.5 ± 4.0 | 42.8 ± 4.3 |
| 4 (Composition 200 (300 mg/kg)) | 50.7 ± 3.0 | 29.4 ± 4.2 | 37.8 ± 3.6 | 42.8 ± 4.4 | 44.7 ± 5.1 | 45.1 ± 5.0 |
| 5 (Composition 200 (400 mg/kg)) | 50.5 ± 3.2 | 29.2 ± 4.4 | 38.5 ± 3.7 | 43.5 ± 4.5 | 45.3 ± 5.2 | 45.7 ± 4.8 |
| 6 (Indomethacin (2 mg/kg)) | 50.9 ± 2.8 | 29.3 ± 4.3 | 37.2 ± 3.8 | 42.1 ± 4.3 | 42.8 ± 4.9 | 44.2 ± 4.7 |

Based on Table 11, MIA injection induced a significant decrease in right-hind-limb weight-bearing (Group 2:29.0±2.8%, p<0.001 vs. normal), confirming successful osteoarthritis establishment. After two weeks of daily oral administration of Composition 200, both the 200 mg/kg (Group 3:36.5±3.5%, p<0.01 vs. Group 2) and 300 mg/kg (Group 4: 37.8±3.6%, p<0.001 vs. Group 2) doses significantly improved weight-bearing, similar to the indomethacin control (Group 6: 37.2±3.8%, p<0.001 vs. Group 2). By Week 6 (Day 49), the 200 mg/kg group reached 41.5±4.0% (p<0.01 vs. Group 2), while the 300 mg/kg and 400 mg/kg (Group 5:45.3±5.2%) doses both exceeded indomethacin (Group 6: 42.8±4.9%) (p<0.001 vs. Group 2). At Week 8 (Day 63), all Composition 200-treated groups (200-400 mg/kg) maintained improvements (42.8±4.3% to 45.7±4.8%) that were statistically indistinguishable from indomethacin (44.2±4.7%, p>0.05). These results demonstrate that oral Composition 200 at 200-400 mg/kg/day restores hind-limb weight-bearing in MIA-induced OA rats, with 300 mg/kg and 400 mg/kg doses matching or slightly surpassing the efficacy of indomethacin by Weeks 6-8.

(B) Histological Scores of Articular Cartilage Degeneration:

TABLE 12

Histological scores of articular cartilage
degeneration (mean ± SD; n = 10)

| Group | Baseline Score | Week 9 Score | % Reduction vs Group 2 | p (vs Group 2) |
|---|---|---|---|---|
| 1 (Control (no MIA)) | 0.0 ± 0.0 | 0.0 ± 0.0 | — | — |

TABLE 12-continued

Histological scores of articular cartilage
degeneration (mean ± SD; n = 10)

| Group | Baseline Score | Week 9 Score | % Reduction vs Group 2 | p (vs Group 2) |
|---|---|---|---|---|
| 2 (OA Model (MIA + vehicle)) | 0.0 ± 0.0 | 18.3 ± 3.0 | — | — |
| 3 (Composition 200 (200 mg/kg)) | 0.0 ± 0.0 | 13.5 ± 2.6 (↓26.2%) | 26.2% | <0.05 |
| 4 (Composition 200 (300 mg/kg)) | 0.0 ± 0.0 | 12.8 ± 2.4 (↓30.1%) | 30.1% | <0.05 |
| 5 (Composition 200 (400 mg/kg)) | 0.0 ± 0.0 | 12.5 ± 2.3 (↓31.7%) | 31.7% | <0.05 |
| 6 (Indomethacin (2 mg/kg)) | 0.0 ± 0.0 | 13.8 ± 2.7 (↓24.6%) | 24.6% | <0.05 |

Based on Table 12, at nine weeks post-MIA injection, the osteoarthritis control group (Group 2) exhibited pronounced synovial hyperplasia with dense inflammatory cell infiltration, cartilage erosion, pannus formation, and subchondral bone damage. In contrast, all three doses of Composition 200 (200, 300, and 400 mg/kg/day) significantly reduced histopathological scores compared to Group 2 (p<0.05). Specifically, at 200 mg/kg (Group 3), the synovial lining was only mildly thickened with fewer inflammatory cells, moderate chondrocyte loss, and reduced pannus. At 300 mg/kg (Group 4), the synovium almost normalized with minimal inflammation, preserved cartilage, and only focal damage. At 400 mg/kg (Group 5), synovial and cartilage architecture closely matched the normal control, with virtually no pannus and minimal subchondral bone damage. These effects equaled or slightly exceeded those of the Indomethacin positive control (Group 6), which showed moderate reduction in synovial hyperplasia, low-level inflammatory infiltration, mild cartilage erosion, and minimal pannus. Among treated groups, the 400 mg/kg dose achieved the greatest cartilage protection (approximately 31.7% reduction in damage), demonstrating superior joint preservation comparable to or better than Indomethacin. Thus, the histological findings confirm that composition 200 provides pronounced joint protection in the MIA-induced osteoarthritis model.

(C) Hematology and Serum Biochemistry:

TABLE 13

Inflammatory markers (mean ± SD; n = 10)

| Group | WBC (×10³/mm³) | LYM (×10³/mm³) | MON (×10³/mm³) | GRA (×10³/mm³) | CRP (mg/L) | RF (mg/L) |
|---|---|---|---|---|---|---|
| Week 1 (Post-MIA, Pre-treatment) | | | | | | |
| 1 (Control) | 3.8 ± 0.1 | 4.1 ± 0.1 | 0.05 ± 0.002 | 0.11 ± 0.002 | — | — |
| 2 (OA Model (MIA + vehicle)) | 9.6 ± 0.1 | 5.6 ± 0.04 | 0.08 ± 0.005 | 0.13 ± 0.004 | 2.4 ± 0.6 | 4.1 ± 0.3 |
| 3 Composition 200 (200 mg/kg) | 8.4 ± 0.1 | 5.7 ± 0.05 | 0.065 ± 0.002 | 0.12 ± 0.004 | 1.8 ± 0.2 | 3.8 ± 0.4 |
| 4 (Composition 200 (300 mg/kg)) | 6.0 ± 0.1 | 4.4 ± 0.07 | 0.065 ± 0.004 | 0.12 ± 0.005 | 1.5 ± 0.3 | 2.6 ± 0.5 |
| 5 (Composition 200 (400 mg/kg)) | 5.9 ± 0.1 | 4.2 ± 0.08 | 0.055 ± 0.007 | 0.11 ± 0.001 | 1.3 ± 0.3 | 1.7 ± 0.6 |
| 6 (Indomethacin (2 mg/kg)) | 4.7 ± 0.1 | 4.1 ± 0.09 | 0.052 ± 0.007 | 0.11 ± 0.002 | 1.7 ± 0.3 | 1.7 ± 0.6 |
| Week 9 (Post-treatment) | | | | | | |
| 1 (Control) | 3.7 ± 0.1 | 4.0 ± 0.1 | 0.05 ± 0.001 | 0.11 ± 0.002 | — | — |
| 2 (OA Model (MIA + vehicle)) | 8.3 ± 0.2 | 5.4 ± 0.05 | 0.08 ± 0.005 | 0.12 ± 0.004 | 2.3 ± 0.3 | 4.1 ± 0.4 |
| 3 Composition 200 (200 mg/kg) | 6.9 ± 0.1 | 4.4 ± 0.06 | 0.063 ± 0.002 | 0.12 ± 0.004 | 1.7 ± 0.2 | 3.7 ± 0.3 |
| 4 (Composition 200 (300 mg/kg)) | 5.8 ± 0.1 | 4.2 ± 0.05 | 0.064 ± 0.003 | 0.12 ± 0.005 | 1.4 ± 0.3 | 2.8 ± 0.4 |
| 5 (Composition 200 (400 mg/kg)) | 5.6 ± 0.1 | 4.1 ± 0.08 | 0.052 ± 0.006 | 0.11 ± 0.002 | 1.2 ± 0.3 | 1.8 ± 0.5 |
| 6 (Indomethacin (2 mg/kg)) | 4.6 ± 0.1 | 4.0 ± 0.09 | 0.052 ± 0.004 | 0.11 ± 0.002 | 1.5 ± 0.3 | 1.6 ± 0.6 |

29

Based on Table 13, at one week post-MIA injection (Week 1), the osteoarthritis control group (Group 2) exhibited marked systemic inflammation, with total leukocyte counts increasing to 9.6±0.1×10³ cells/mm³ (p<0.001 vs. normal), lymphocytes to 5.5±0.04×10³ cells/mm³, monocytes to 0.08±0.005×10³ cells/mm³, and granulocytes to 0.13±0.04× 10³ cells/mm³, alongside elevated CRP (2.4±0.6 mg/L) and RF (4.1±0.3 mg/L). After eight weeks of daily oral administration of Composition 200 at 200, 300, and 400 mg/kg, all treated groups demonstrated significant reductions in WBC, lymphocytes, monocytes, granulocytes, CRP, and RF compared to Group 2 (p<0.05-0.01). Specifically, at 400 mg/kg, total leukocytes fell to 4.9±0.4×10³ cells/mm³, lymphocytes to 4.1±0.09×10³ cells/mm³, monocytes to 0.05±0.003×10³ cells/mm³, granulocytes to 0.12±0.003×10³ cells/mm³, CRP to 1.2±0.4 mg/L, and RF to 1.7±0.43 mg/L-values that were statistically indistinguishable from those achieved by indomethacin and approximated normal control levels (p>0.05). These findings confirm that Composition 200 (300-400 mg/kg/day) effectively normalizes hematological and biochemical inflammatory markers in MIA-induced osteoarthritis.

Example 5. Evaluation of Synergistic Efficacy of Oral Composition 200 and Topical Composition in an MIA-Induced Rat Osteoarthritis Model

(I) Materials and Methods (A) Animals: Male Sprague-Dawley rats (8-10 weeks old; 200-220 g) were obtained and housed four per cage under controlled conditions (22±2° C.; 50%-60% humidity; 12 h light/12 h dark) with ad libitum access to standard chow and reverse-osmosis water. All rats were acclimated for 7 days prior to experimental procedures.

(B) OA Induction: On Day 0, each rat received a 50 μL intra-articular injection of 2 mg monosodium iodoacetate (MIA; in sterile saline) into the right knee under light isoflurane anesthesia. Animals were returned to their cages for recovery and free movement.

(C) Treatments & group allocation (n=6 per group):
Test Sample:
Composition 200 according to formulation 2 of example 1;
Topical composition refers to composition as described in patent application Ser. No. 19/275,921, entitled "Plant-based extract complex composition having the properties for supporting the relief of musculoskeletal pain, antibacterial and anti-inflammatory and process of manufacturing the same", filed on 21 Jul. 2025;
Beginning 24 h post-MIA (Day 1), treatments were administered once daily for 8 weeks (Days 1-56). Rats were randomly divided into three groups (n=6 per group).

TABLE 14

Treatment groups and dosing regimens

| Group | Description | Oral (Composition 200) | Topical composition |
|---|---|---|---|
| 1 | OA Control (Vehicle) | 0.9% saline, 10 mL/kg by oral gavage | Vehicle gel (no active), 100 μL/day |
| 2 | Composition 200 Monotherapy | 300 mg/kg/day in 0.9% saline, 10 mL/kg PO | Vehicle gel, 100 μL/day |

30

TABLE 14-continued

Treatment groups and dosing regimens

| Group | Description | Oral (Composition 200) | Topical composition |
|---|---|---|---|
| 3 | Combination (Composition 200 + Topical composition) | 300 mg/kg/day in 0.9% saline, 10 mL/kg PO | 100 mg active in 100 μL gel/day | in which:
composition 200: suspended in 0.9% saline at 30 mg/mL, dosed at 10 mL/kg to achieve 300 mg/kg;
topical composition: Topical gel containing 1 mg active extract per μL; 100 μL delivers 100 mg active. Vehicle gel has identical base without extract.

(D) Key Endpoints & Measurements:
(a) Pain & Inflammation (Weeks 0, 2, 4, 6, 8):
Hind-Limb Weight Bearing (%): Assessed using an incapacitance tester; three consecutive readings per session were averaged;
Knee Joint Diameter (cm): Measured at the mid-patella using a digital vernier caliper;
Hind-Paw Volume (mL): Determined via water plethysmometer by immersing the hind paw to the tibiotarsal junction;
Arthritis Severity Score (0-4):
0=no visible swelling;
1=mild swelling/redness of ankle;
2=moderate swelling to midfoot;
3=marked swelling with redness;
4=severe swelling with joint deformity.
(b) Inflammatory Biomarkers (Day 56):
Total WBC (×10³ cells/mm³) and Differential WBC (lymphocytes, monocytes, granulocytes) via automated hematology analyzer;
C-Reactive Protein (CRP, mg/L) and Rheumatoid Factor (RF, mg/L) quantified by rat-specific ELISA kits according to manufacturer protocols.
(c) Histopathology of Ankle Joint (Day 56):
Tissue Collection & Processing: Right knee joints were fixed in 10% neutral buffered formalin, decalcified in 10% EDTA for three weeks, then paraffin-embedded;
Sectioning & Staining: 5 μm sections were stained with hematoxylin and eosin;
Scoring (0-3 per category; total 0-12): histopathological evaluation was performed by examining four key features: synovial inflammation; pannus formation; cartilage erosion; subchondral bone damage.

(II) Results (Week 8)

TABLE 15

Summary of clinical, hematological, biochemical, and histopathological outcomes at week 8

| Parameter | Group 1 | Group 2 | Group 4 |
|---|---|---|---|
| Weight bearing (%) | 32 ± 3 | 42 ± 3 | 50 ± 3 |
| Knee diameter (cm) | 0.95 ± 0.04 | 0.75 ± 0.03 | 0.68 ± 0.03 |
| Hind-paw volume (mL) | 1.02 ± 0.06 | 0.72 ± 0.05 | 0.60 ± 0.05 |
| Arthritis score (0-4) | 3.2 ± 0.4 | 1.5 ± 0.3 | 0.8 ± 0.2 |
| Total WBC (×10³/mm³) | 10.5 ± 0.8 | 6.2 ± 0.6 | 4.8 ± 0.4 |
| CRP (mg/L) | 2.8 ± 0.4 | 1.4 ± 0.3 | 0.9 ± 0.2 |
| RF (mg/L) | 4.5 ± 0.5 | 2.1 ± 0.4 | 1.2 ± 0.3 |
| Histopathology score (0-12) | 9.2 ± 0.9 | 5.1 ± 0.5 | 2.8 ± 0.4 |

Based on Table 15, the combination of oral composition 200 and topical composition (Group 3) achieved markedly superior improvements in weight bearing, joint diameter, hind-paw volume, arthritis score, inflammatory biomarkers (WBC, CRP, RF), and histopathological joint preservation compared to both the vehicle group (Group 1) and the oral monotherapy group (Group 2). Specifically, Group 3's weight bearing (50%±3%) and reductions in knee diameter (0.68±0.03 cm) and hind-paw volume (0.60+0.05 mL) were significantly better than in Group 2 (p<0.05). Inflammatory markers likewise decreased most robustly under combination treatment: total WBC fell to $4.8\pm0.4\times10^3/mm^3$, CRP to 0.9±0.2 mg/L, and RF to 1.2±0.3 mg/L (all p<0.05 vs. Group 2). Histopathological scores confirmed minimal synovial inflammation, negligible pannus, and preserved cartilage in Group 3 (mean 2.8±0.4), whereas Group 2 still showed moderate joint damage (5.1±0.5) and Group 1 was severely affected (9.2±0.9).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, element components, and/or groups thereof.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order, or steps may be added, deleted, or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method of manufacturing a herbal oral composition having the properties for supporting and enhancing musculoskeletal health, comprising the following steps (i) to (vi):

(i) preparing materials including: a herbal concentrate having a first percentage (%) by weight, a herbal powder mixture having a second percentage (%) by weight, a mushroom extract ingredient having a third percentage (%) by weight, a collagen extract ingredient having a fourth percentage (%) by weight, a solution containing 4-allylpyrocatechol having a fifth percentage (%) by weight, and a plant-derived nanovesicles ingredient having a sixth percentage (%) by weight; wherein the percentage (%) by weight is determined by the sum from the first percentage (%) to the sixth percentage (%);

wherein the preparing of the herbal concentrate comprises the steps of:

(a1) collecting and pre-processing 19 medicine herbals to be extracted individually including washing, drying overnight and drying at 40° C.-50° C. until reaching 8%-15% moisture, chopping and storing in separate instruments;

wherein the 19 medicine herbals include: *Angelica pubescens* root, *Cinnamomum cassia* branch, *Asarum heterotropoides* root, *Ligusticum wallichii* rhizome, *Angelica sinensis* root, *Saposhnikovia divaricata* root, *Eucommia ulmoides* bark, *Achyranthes bidentata* root, *Wolfiporia extensa* fruiting body, *Glycyrrhiza uralensis* root, *Loranthus parasiticus* branch, *Paeonia lactiflora* root, *Rehmannia glutinosa* root, *Justicia gendarussa* root, *Tinospora sinensis* stem and leaves, *Chrysanthemum indicum* flower, *Vitex negundo* leaves, *Brassica alba* seed, and *Justicia gendarussa* bark;

(a2) creating a medicine herbal mixture by mixing 19 medicine herbals prepared in step (a1) in the following percentage (%) by weight: 2.25 parts of *Angelica pubescens*, 1.5 parts of *Cinnamomum cassia*, 1.5 parts of *Asarum heterotropoides*, 1.5 parts of *Ligusticum wallichii*, 1.5 parts of *Angelica sinensis*, 2 parts of *Saposhnikovia* divaricata, 1.5 parts of *Eucommia ulmoides*, 2.25 parts of *Achyranthes* bidentata, 1.5 parts of *Poria* cocos, 1.5 parts of *Glycyrrhiza uralensis*, 1.5 parts of *Loranthus* parasiticus, 1.5 parts of *Paeonia lactiflora*, 1.5 parts of *Rehmannia* glutinosa, 1.5 parts of *Justicia gendarussa*, 1.2 parts of *Tinospora sinensis*, 1.2 parts of *Chrysanthemum indicum*, 0.5-1 parts of *Vitex negundo*, 0.5-1.5 parts *Brassica alba*, and 0.5-1 parts of *Justicia gendarussa*; and (a3) creating the herbal concentrate by soaking the medicine herbal mixture by mixing the medicine herbal mixture with water in a ratio of 1:15-20 w/v, extracting at 65° C.-70° C. for 3-4 hours to obtain a mixture 1, centrifuging the mixture 1 at a speed of 3000-4000 rpm for 30-40 minutes to obtain a centrifuged solution 1 and a residue 1; soaking the residue 1 with water and cellulase in a ratio of 1000:5000:(1-2) w/v/w, incubating at 45° C.-50° C. for 2-3 hours to obtain a mixture 2, centrifuging the mixture 2 at a speed of 3000-4000 rpm for 30-40 minutes to obtain a centrifuged solution 2 and a residue 2; soaking the residue 2 with ethanol 60% in a ratio of 1:10 w/v, stirring 600-700 rpm and support ultrasonic waves at frequency 0.2-0.3 kHz to obtain a mixture 3, centrifuging the mixture 3 at a speed of 3000-4000 rpm for 30-40 minutes to obtain a centrifuged solution 3 and a residue 3; mixing the centrifuged solution with the centrifuged solution 2, and the centrifuged solution 3 to obtain a centrifuged mixture; and evaporating the centrifuged mixture at 45° C.-50° C., pressure of 100-150 mbar until the humidity reaches 25%-30% to obtain the herbal concentrate;

wherein the preparing of the herbal powder mixture comprises the steps of:

(b1) collecting and pre-processing 17 medicine herbals to be used individually including removing damaged parts, washing, drying overnight and drying at 40° C.-50° C. until reaching 8%-15% moisture, chopping, grinding into powder and storing in separate instruments;

wherein 17 medicine herbal powders include: *Angelica pubescens* uses the root parts, *Cinnamomum cassia* uses the branch parts, *Asarum heterotropoides* uses the root parts, *Ligusticum wallichii* uses the rhizome parts, *Angelica sinensis* uses the root parts, *Saposhnikovia divaricata* uses the root parts, *Eucommia ulmoides* uses the bark parts, *Achyranthes bidentata* uses the root parts, *Wolfiporia extensa* uses the fruiting body parts, *Glycyrrhiza uralensis* uses the root parts, *Loranthus parasiticus* uses the branch parts, *Paeonia lactiflora* uses the root parts, *Rehmannia glutinosa* uses the root parts, *Justicia gendarussa* uses the root parts, *Tinospora sinensis* uses the stem and leaves, *Brassica alba* uses the seed, and *Chrysanthemum indicum* use the flower; and (b2) creating the herbal powder mixture by admixing 17 medicine herbals prepared in step (b1) in the following percentage (%) by weight: 2.25 parts of *Angelica pubescens,* 1.5 parts of *Cinnamomum cassia,* 1.5 parts of *Asarum heterotropoides,* 1.5 parts of *Ligusticum wallichii,* 1.5 parts of *Angelica sinensis,* 2 parts of *Saposhnikovia* divaricata, 1.5 parts of *Eucommia ulmoides,* 2.25 parts of *Achyranthes bidentata,* 1.5 parts of *Poria* cocos, 1.5 parts of *Glycyrrhiza uralensis,* 1.5 parts of *Loranthus parasiticus,* 1.5 parts of *Paeonia lactiflora,* 1.5 parts of *Rehmannia glutinosa,* 1.5 parts of *Justicia gendarussa,* 1.2 parts of *Tinospora sinensis,* 0.5-1.5 parts *Brassica alba*, and 1.2 parts of *Chrysanthemum indicum;* wherein the preparing of the mushroom extract ingredient comprises the steps of:

(c1) collecting and pre-processing four mushrooms to be extracted individually including removing damaged parts, washing, drying at 40° C.-50° C. until reaching 8%-15% moisture, chopping, and storing in separate instruments; wherein four mushrooms include *Auricularia auricula, Tremella fuciformis, Lentinus edodes,* and *Hericium erinaceus;*

(c2) creating a mushroom mixture by admixing four mushrooms prepared in step (c1) in the following percentage (%) by weight: 1-2 parts *Auricularia auricula,* 1-2 parts *Tremella fuciformis,* 1-2 parts *Lentinus edodes*, and 1-2 parts *Hericium erinaceus;*

(c3) mixing the mushroom mixture with water, cellulase, and β-glucanase in a ratio of 1000:10000: 1:1, then incubating at 45° C.-50° C. for 1 hours, and filtering to obtain a treated mushroom mixture; and (c4) grinding the treated mushroom mixture, heating at 70° C. for 2 hours, cooling and freeze-drying to obtain a freeze-dried powder, soaking the freeze-dried powder with ethanol 70% in a ratio of 9:200 w/v, supported ultrasonic waves at a frequency of 0.2-0.3 kHz for 90 minutes to obtain a temporary mixture 1, centrifuging the temporary mixture 1 at a speed of 3000-4000 rpm for 30-40 minutes to obtain a temporary solution 1 and a temporary residue 1; soaking the temporary residue 1 with ethanol 70% in a ratio of 1:13 w/v, supported ultrasonic waves at a frequency of 0.2-0.3 kHz for 60 minutes to obtain a temporary mixture 2, centrifuging the temporary mixture 2 at a speed of 3000-4000 rpm for 30-40 minutes to obtain a temporary solution 2 and a temporary residue 2; soaking the temporary residue 2 with ethanol 70% in a ratio of 1:7 w/v, supported ultrasonic waves at a frequency of 0.2-0.3 kHz for 30 minutes to obtain a temporary mixture 3, centrifuging the temporary mixture 3 at a speed of 3000-4000 rpm for 30-40 minutes to obtain a temporary solution 3 and a temporary residue 3; mixing the temporary solution 1 with the temporary solution 2, and the temporary solution 3 to obtain a base mixture; incubating the base mixture for 3 hours, and evaporating at 45° C.-50° C. with pressure of 100-150 mbar until the humidity reaches 25%-30% to obtain the mushroom extract ingredient;

wherein the preparing of the collagen extract ingredient comprises the steps of:

(d1) collecting by-products from herring including scales, skin and bones in a mass ratio of 1:4:3; wash, drying and grinding into a powder 1;

(d2) soaking the powder 1 with solution NaOH 0.09 M at 4° C. for 3 hours in a ratio of 1:7 w/v, centrifuging at a speed of 8000 rpm for 20 minutes to obtain a solid 1, and washing the solid 1 with water twice;

(d3) soaking the solid 1 at step (d1) with butyl alcohol solution 13% for 45 minutes in a ratio of 1:15 w/v, centrifuging at a speed of 8000 rpm for 20 minutes to obtain a solid 2, and washing the solid 2 with water twice;

(d4) soaking the solid 2 with $H_2O_2$ solution 5% in a ratio of 1:5 w/v for 10 minutes, centrifuging at a speed of 8000 rpm for 20 minutes to obtain a solid 3, and washing the solid 3 with water twice; and (d5) soaking the solid 3 with a pineapple and papaya juice mixture in a ratio of 1:3 w/v for 1 hours, supported ultrasonic waves at a frequency of 0.2-0.3 kHz for 60 minutes, adding pepsin solution 0.45% mixed in 0.6 M acetic acid at 2.5° C.-3° C. for 24 hours according to 1 part of the solid 3:8 parts of pepsin solution w/v, centrifuging at a speed of 8000 rpm at 4° C. for 20 minutes to obtain a supernatant, adjusting pH to 6.8-7.2 with tris base 0.5 M, then precipitate with 2.5 M NaCl solution, and centrifuging at 8000 rpm at 4° C. for 20 min to form precipitate; dissolving the precipitate in 0.5 M acetic acid, dialyzing in 0.1 M acetic acid and distilling water for 48-72 hours, and freeze-drying to obtain the collagen extract ingredient;

wherein the preparing of the solution containing 4-allylpyrocatechol comprises the steps of:

(e1) grinding betel leaves with water in a ratio of 1:5 w/v, treating the ground betel leaves by ultrasonically at a frequency of 0.1 kHz for 2 hours, and steam distilled for 2.5 hours to obtain an extract solution 1 and a remaining solution after distillation;

(e2) mixing the remaining solution after distillation with diethyl ester solution in a ratio of 1:(1-5) v/v, evaporating the centrifuged mixture at 45° C.-50° C., pressure of 100-150 mbar until the humidity reaches 25%-30% to obtain a concentrate; purifying the concentrate through silica gel column chromatography with a hexane-ethyl acetate solvent in a ratio of 9:1, then purifying again one more on a C18 column with MeOH:$H_2O$ fraction in a ratio of 1:1 to obtain a white solid which is 4-allylpyrocatechol compound; and (e3) dissolving the extract solution 1 at step (e1) with the white solid obtained in step (e2) at temperatures of 30° C.-42° C., with stirring at an average speed of 400 rpm for 15 minutes to obtain the solution containing 4-allylpyrocatechol;

wherein the plant-derived nanovesicles ingredient is prepared by mixing a first nanovesicles ingredient with a second nanovesicles ingredient in a ratio of 2:3 w/w;

wherein the preparing of the first nanovesicles ingredient comprises the steps of:

(f1) collecting a plant mixture consisting of 2 parts of *Illicium verum* Hook. f., 3 parts of *Artemisia vulgaris*, and 3 parts of *Piper sarmentosum;*

(f2) washing three times with deionized water at 20° C.-25° C.;

(f3) pureeing the washed plant mixture with phosphate buffer solution (PBS) in a ratio of 1:3 w/v at a speed of 7000-8000 rpm for 15 minutes to obtain a first temporary solution;

(f4) filtering the first temporary solution by a filter membrane with a diameter 0.20-0.22 μm to obtain a second temporary solution;

(f5) centrifuging the second temporary solution by ultracentrifugation at 120000×g for 100 min at 4° C. to obtain a temporary solid;

(f6) dissolving the temporary solid in phosphate buffer solution (PBS), transferring to a 45% sucrose gradient solution, and ultracentrifugation at 130000×g for 100 min to obtain a third temporary solution;

(f7) washing the third temporary solution with PBS and centrifuging at 150000×g for 60 min at 4° C. to obtain a fourth temporary solution; and (f8) filtering the fourth temporary solution through a filter membrane with a diameter 0.20-0.22 μm to obtain the first nanovesicles ingredient;

wherein the preparing of the second nanovesicles ingredient comprises the steps of:

(g1) collecting a fruit mixture including 3 parts of dragon fruit, 3 parts of avocado, and 1 part of watermelon;

(g2) washing the fruit mixture three times with deionized water at 20° C.-25° C.;

(g3) pureeing the washed fruit mixture with phosphate buffer solution (PBS) in a ratio of 1:1 (g/mL) at a speed of 7000-8000 rpm for 15 minutes to obtain a first foundation solution;

(g4) filtering the first foundation solution by a filter membrane with a diameter 0.20-0.22 μm to obtain a second foundation solution;

(g5) centrifuging the second foundation solution by ultracentrifugation at 100000×g for 60 min to obtain a residue;

(g6) dissolving the residue in phosphate buffer solution (PBS), transferring to a 45% sucrose gradient solution, and ultracentrifugation at 130000×g for 100 min to obtain a third foundation solution;

(g7) stirring the third foundation solution with a 10% polyethylene glycol-8000 (PEG8000) solution in a ratio of 1:1 v/v, and incubating for 8-10 hours at 4° C., then centrifuging at 110000×g for 40 minutes at 4° C. to obtain a precipitate;

(g8) dissolving the precipitate in phosphate buffer solution (PBS) in a ratio of 1:2 w/v to obtain a foundation solution; and (g9) filtering the foundation solution by a tangential flow filtration (TFF) to obtain the second nanovesicles ingredient; wherein the TFF comprises a molecular size of 500 kDa, and filtering at a flow rate of 20 mL/min with the transmembrane pressure maintained at 2 bar;

(ii) mixing the solution containing 4-allylpyrocatechol with the plant-derived nanovesicles ingredient at temperatures of 30° C.-50° C., with stirring at an average speed of 400 rpm for 15 minutes to obtain a solution 10;

(iii) mixing the herbal concentrate with the herbal powder mixture, the mushroom extract ingredient, the collagen extract ingredient, and the solution 10 at temperatures of 30° C.-50° C., with stirring at an average speed of 400 rpm for 15-45 minutes to obtain a foundation mixture;

(iv) creating a herbal oral composition, wherein 100 mL of the herbal oral composition created by mixing performed in a specific order from (h1) to (h3) comprising:

(h1) adding 125 mg of the foundation mixture with 100 mg of glycyrrhizic acid, 50 mg of a phospholipid component, and 315 mg of lipoid S100 into a reaction tank, adding 0.2 part of absolute ethanol, refluxing at 60° C. for 2 hours to obtain a solution 20;

(h2) dissolving 250 mg of chitosan with 10 mL of distilled water, slowly adding 0.5 mL of glacial acetic acid, combined with stirring 50 rpm, adding 30 ml of water and let stand until the solution is clear, transferring the cleared solution into a 50 mL volumetric flask, and adding distilled water to the mark to obtain 50 mL of a chitosan solution with concentration of 5 mg/ml; and (h3) dissolving 1 mL of the chitosan solution at step (h2) with 300 mg of a poloxamer component and 85 mL of distilled water, cooling the reaction mixture and stirring at 600 rpm until the reaction mixture is homogeneous, injecting 8 mL of the solution 10 at a rate of 1 mL/min with a stirring speed of 1000 rpm for 30 minutes, and adding distilled water to make 100 mL of the herbal oral composition having the properties for supporting and enhancing musculoskeletal health.

2. The method of claim 1, wherein the by-products from herring is selected from the one or more in the genus *Sardinella* of the including *Sardinella aurita, Sardinella jussieu, Sardinella albella, Sardinella atricauda, Sardinella brachysoma, Sardinella fijiense, Sardinella fimbriata, Sardinella hualiensis, Sardinella marquesensis*, and *Sardinella melanura.*

3. The method of claim 1, wherein the poloxamer component is selected from the group consisting of poloxamer 124, poloxamer 188, poloxamer 237, poloxamer 338, and poloxamer 407.

4. The method of claim 1, wherein the phospholipid component is selected from the group consisting of phosphatidylcholine (DMPC), phosphatidylserine (PS), and phosphatidylethanolamine (PE).

5. The method of claim 1, wherein the pineapple and papaya juice mixture is prepared by mixing a pineapple juice with a papaya juice in a ratio of (1-5):(1-5) v/v.

6. The method of claim 1, wherein said first percentage (%) by weight is between 25% to 60%, said second percentage (%) by weight is between 20% to 60%, said third percentage (%) by weight is between 0.5% to 18%, said fourth percentage (%) by weight is between 0.1% to 20%, said fifth percentage (%) by weight is between 0.01% to 0.45%, and said sixth percentage (%) by weight is between 0.02% to 0.2% of the total weight of said foundation mixture.

7. The method of claim 6, wherein said first percentage (%) by weight is between 30% to 60%, said second percentage (%) by weight is between 30% to 60%, said third percentage (%) by weight is between 1.5% to 18%, said fourth percentage (%) by weight is between 2.5% to 20%, and said fifth percentage (%) by weight is between 0.01% to 0.45%, and said sixth percentage (%) by weight is between 0.02% to 0.2% of the total weight of said foundation mixture.

8. The method of claim 1, wherein the method further comprises mixing the herbal oral composition with an excipient ingredient in a ratio of 1:(12-30) w/w, and evaporating the centrifuged mixture at 45° C.-50° C., pressure of 100-150 mbar until the humidity reaches 10%-20%; wherein the excipient ingredient is prepared by mixing corn starch, lactose, talc, nipagin, propylparaben and magnesium stearate in the ratio of 3.5:1.5:2.5:1: 1:1.5 by mass.

9. A herbal oral composition having the properties for supporting and enhancing musculoskeletal health comprising: a herbal concentrate having a first percentage (%) by weight, a herbal powder mixture having a second percentage (%) by weight, a mushroom extract ingredient having a third percentage (%) by weight, a collagen extract ingredient having a fourth percentage (%) by weight, a solution containing 4-allylpyrocatechol having a fifth percentage (%) by weight, and a plant-derived nanovesicles ingredient having a sixth percentage (%) by weight; wherein the percentage (%) by weight is determined by the sum from the first percentage (%) to the sixth percentage (%); wherein said herbal composition is produced by a process comprising the following steps:

(i) preparing materials including: the herbal concentrate, the herbal powder mixture, the mushroom extract ingredient, the collagen extract ingredient, the solution containing 4-allylpyrocatechol, and the plant-derived nanovesicles ingredient;

wherein the preparing of the herbal concentrate comprises the steps of:

(a1) collecting and pre-processing 19 medicine herbals to be extracted individually including washing, drying overnight and drying at 40° C.-50° C. until reaching 8%-15% moisture, chopping and storing in separate instruments;

wherein 19 medicine herbals include: *Angelica pubescens* root, *Cinnamomum cassia* branch, *Asarum heterotropoides* root, *Ligusticum wallichii* rhizome, *Angelica sinensis* root, *Saposhnikovia*

*divaricata* root, *Eucommia ulmoides* bark, *Achyranthes bidentata* root, *Wolfiporia extensa* fruiting body, *Glycyrrhiza uralensis* root, *Loranthus parasiticus* branch, *Paeonia lactiflora* root, *Rehmannia glutinosa* root, *Justicia gendarussa* root, *Tinospora sinensis* stem and leaves, *Chrysanthemum indicum* flower, *Vitex negundo* leaves, *Brassica alba* seed, and *Justicia gendarussa* bark;

(a2) creating a medicine herbal mixture by mixing 19 medicine herbals prepared in step (a1) in the following percentage (%) by weight: 2.25 parts of *Angelica pubescens*, 1.5 parts of *Cinnamomum cassia*, 1.5 parts of *Asarum heterotropoides*, 1.5 parts of *Ligusticum wallichii*, 1.5 parts of *Angelica sinensis*, 2 parts of *Saposhnikovia divaricata*, 1.5 parts of *Eucommia ulmoides*, 2.25 parts of *Achyranthes bidentata*, 1.5 parts of *Poria cocos*, 1.5 parts of *Glycyrrhiza uralensis*, 1.5 parts of *Loranthus parasiticus*, 1.5 parts of *Paeonia lactiflora*, 1.5 parts of *Rehmannia glutinosa*, 1.5 parts of *Justicia gendarussa*, 1.2 parts of *Tinospora sinensis*, 1.2 parts of *Chrysanthemum indicum*, 0.5-1 parts of *Vitex negundo*, 0.5-1.5 parts *Brassica alba*, and 0.5-1 parts of *Justicia gendarussa*; and (a3) creating the herbal concentrate by soaking the medicine herbal mixture by mixing the medicine herbal mixture with water in a ratio of 1:15-20 w/v, extracting at 65° C.-70° C. for 3-4 hours to obtain a mixture 1, centrifuging the mixture 1 at a speed of 3000-4000 rpm for 30-40 minutes to obtain a centrifuged solution 1 and a residue 1; soaking the residue 1 with water and cellulase in a ratio of 1000:5000:(1-2) w/v/w, incubating at 45° C.-50° C. for 2-3 hours to obtain a mixture 2, centrifuging the mixture 2 at a speed of 3000-4000 rpm for 30-40 minutes to obtain a centrifuged solution 2 and a residue 2; soaking the residue 2 with ethanol 60% in a ratio of 1:10 w/v, stirring 600-700 rpm and support ultrasonic waves at frequency 0.2-0.3 kHz to obtain a mixture 3, centrifuging the mixture 3 at a speed of 3000-4000 rpm for 30-40 minutes to obtain a centrifuged solution 3 and a residue 3; mixing the centrifuged solution with the centrifuged solution 2, and the centrifuged solution 3 to obtain a centrifuged mixture; and evaporating the centrifuged mixture at 45° C.-50° C., pressure of 100-150 mbar until the humidity reaches 25%-30% to obtain the herbal concentrate;

wherein the preparing of the herbal powder mixture comprises the steps of:

(b1) collecting and pre-processing 17 medicine herbals to be used individually including removing damaged parts, washing, drying overnight and drying at 40° C.-50° C. until reaching 8%-15% moisture, chopping, grinding into powder and storing in separate instruments;

wherein 17 medicine herbal powders include: *Angelica pubescens* uses the root parts, *Cinnamomum cassia* uses the branch parts, *Asarum heterotropoides* uses the root parts, *Ligusticum wallichii* uses the rhizome parts, *Angelica sinensis* uses the root parts, *Saposhnikovia divaricata* uses the root parts, *Eucommia ulmoides* uses the bark parts, *Achyranthes bidentata* uses the root parts, *Wolfiporia extensa* uses the fruiting body parts, *Glycyrrhiza uralensis* uses the root parts, *Loranthus parasiticus* uses the branch parts, *Paeo-*

*nia lactiflora* uses the root parts, *Rehmannia glutinosa* uses the root parts, *Justicia gendarussa* uses the root parts, *Tinospora sinensis* uses the stem and leaves, *Brassica alba* uses the seed, and *Chrysanthemum indicum* use the flower; and (b2) creating the herbal powder mixture by admixing 17 medicine herbals prepared in step (b1) in the following percentage (%) by weight: 2.25 parts of *Angelica pubescens,* 1.5 parts of *Cinnamomum cassia,* 1.5 parts of *Asarum heterotropoides,* 1.5 parts of *Ligusticum wallichii,* 1.5 parts of *Angelica sinensis,* 2 parts of *Saposhnikovia divaricata,* 1.5 parts of *Eucommia ulmoides,* 2.25 parts of *Achyranthes bidentata,* 1.5 parts of *Poria cocos,* 1.5 parts of *Glycyrrhiza uralensis,* 1.5 parts of *Loranthus parasiticus,* 1.5 parts of *Paeonia lactiflora,* 1.5 parts of *Rehmannia glutinosa,* 1.5 parts of *Justicia gendarussa,* 1.2 parts of *Tinospora sinensis,* 0.5-1.5 parts *Brassica alba,* and 1.2 parts of *Chrysanthemum indicum;* wherein the preparing of the mushroom extract ingredient comprises the steps of:

(c1) collecting and pre-processing four mushrooms to be extracted individually including removing damaged parts, washing, drying at 40° C.-50° C. until reaching 8%-15% moisture, chopping, and storing in separate instruments; wherein four mushrooms include *Auricularia auricula, Tremella fuciformis, Lentinus edodes,* and *Hericium erinaceus;*

(c2) creating a mushroom mixture by admixing four mushrooms prepared in step (c1) in the following percentage (%) by weight: 1-2 parts *Auricularia auricula,* 1-2 parts *Tremella fuciformis,* 1-2 parts *Lentinus edodes,* and 1-2 parts *Hericium erinaceus;*

(c3) mixing the mushroom mixture with water, cellulase, and β-glucanase in a ratio of 1000:10000:1:1, then incubating at 45° C.-50° C. for 1 hours, and filtering to obtain a treated mushroom mixture; and (c4) grinding the treated mushroom mixture, heating at 70° C. for 2 hours, cooling and freeze-drying to obtain a freeze-dried powder, soaking the freeze-dried powder with ethanol 70% in a ratio of 9:200 w/v, supported ultrasonic waves at a frequency of 0.2-0.3 kHz for 90 minutes to obtain a temporary mixture 1, centrifuging the temporary mixture 1 at a speed of 3000-4000 rpm for 30-40 minutes to obtain a temporary solution 1 and a temporary residue 1; soaking the temporary residue 1 with ethanol 70% in a ratio of 1:13 w/v, supported ultrasonic waves at a frequency of 0.2-0.3 kHz for 60 minutes to obtain a temporary mixture 2, centrifuging the temporary mixture 2 at a speed of 3000-4000 rpm for 30-40 minutes to obtain a temporary solution 2 and a temporary residue 2; soaking the temporary residue 2 with ethanol 70% in a ratio of 1:7 w/v, supported ultrasonic waves at a frequency of 0.2-0.3 kHz for 30 minutes to obtain a temporary mixture 3, centrifuging the temporary mixture 3 at a speed of 3000-4000 rpm for 30-40 minutes to obtain a temporary solution 3 and a temporary residue 3; mixing the temporary solution 1 with the temporary solution 2, and the temporary solution 3 to obtain a base mixture; incubating the base mixture for 3 hours, and evaporating at 45° C.-50° C. with pressure of 100-150 mbar until the humidity reaches 25%-30% to obtain the mushroom extract ingredient;

wherein the preparing of the collagen extract ingredient comprises the steps of:

(d1) collecting by-products from herring including scales, skin and bones in a mass ratio of 1:4:3; wash, drying and grinding into a powder 1;

(d2) soaking the powder 1 with solution NaOH 0.09 M at 4° C. for 3 hours in a ratio of 1:7 w/v, centrifuging at a speed of 8000 rpm for 20 minutes to obtain a solid 1, and washing the solid 1 with water twice;

(d3) soaking the solid 1 at step (d1) with butyl alcohol solution 13% for 45 minutes in a ratio of 1:15 w/v, centrifuging at a speed of 8000 rpm for 20 minutes to obtain a solid 2, and washing the solid 2 with water twice;

(d4) soaking the solid 2 with $H_2O_2$ solution 5% in a ratio of 1:5 w/v for 10 minutes, centrifuging at a speed of 8000 rpm for 20 minutes to obtain a solid 3, and washing the solid 3 with water twice; and (d5) soaking the solid 3 with a pineapple and papaya juice mixture in a ratio of 1:3 w/v for 1 hours, supported ultrasonic waves at a frequency of 0.2-0.3 kHz for 60 minutes, adding pepsin solution 0.45% mixed in 0.6 M acetic acid at 2.5° C.-3° C. for 24 hours according to 1 part of the solid 3:8 parts of pepsin solution w/v, centrifuging at a speed of 8000 rpm at 4° C. for 20 minutes to obtain a supernatant, adjusting pH to 6.8-7.2 with tris base 0.5 M, then precipitate with 2.5 M NaCl solution, and centrifuging at 8000 rpm at 4° C. for 20 min to form precipitate; dissolving the precipitate in 0.5 M acetic acid, dialyzing in 0.1 M acetic acid and distilling water for 48-72 hours, and freeze-drying to obtain the collagen extract ingredient;

wherein the preparing of the solution containing 4-allylpyrocatechol comprises the steps of:

(e1) grinding betel leaves with water in a ratio of 1:5 w/v, treating the ground betel leaves by ultrasonically at a frequency of 0.1 kHz for 2 hours, and steam distilled for 2.5 hours to obtain an extract solution 1 and a remaining solution after distillation;

(e2) mixing the remaining solution after distillation with diethyl ester solution in a ratio of 1:(1-5) v/v, evaporating the centrifuged mixture at 45° C.-50° C., pressure of 100-150 mbar until the humidity reaches 25%-30% to obtain a concentrate; purifying the concentrate through silica gel column chromatography with a hexane-ethyl acetate solvent in a ratio of 9:1, then purifying again one more on a C18 column with MeOH:$H_2O$ fraction in a ratio of 1:1 to obtain a white solid which is 4-allylpyrocatechol compound; and (e3) dissolving the extract solution 1 at step (e1) with the white solid obtained in step (e2) at temperatures of 30° C.-42° C., with stirring at an average speed of 400 rpm for 15 minutes to obtain the solution containing 4-allylpyrocatechol;

wherein the plant-derived nanovesicles ingredient is prepared by mixing a first nanovesicles ingredient with a second nanovesicles ingredient in a ratio of 2:3 w/w;

wherein the preparing of the first nanovesicles ingredient comprises the steps of:

(f1) collecting a plant mixture consisting of 2 parts of *Illicium verum* Hook., 3 parts of *Artemisia vulgaris,* and 3 parts of *Piper sarmentosum;*

(f2) washing three times with deionized water at 20° C.-25° C.;

(f3) pureeing the washed plant mixture with phosphate buffer solution (PBS) in a ratio of 1:3 w/v at a speed of 7000-8000 rpm for 15 minutes to obtain a first temporary solution;

(f4) filtering the first temporary solution by a filter membrane with a diameter 0.20-0.22 μm to obtain a second temporary solution;

(f5) centrifuging the second temporary solution by ultracentrifugation at 120000×g for 100 min at 4° C. to obtain a temporary solid;

(f6) dissolving the temporary solid in phosphate buffer solution (PBS), transferring to a 45% sucrose gradient solution, and ultracentrifugation at 130000×g for 100 min to obtain a third temporary solution;

(f7) washing the third temporary solution with PBS and centrifuging at 150000×g for 60 min at 4° C. to obtain a fourth temporary solution; and (f8) filtering the fourth temporary solution through a filter membrane with a diameter 0.20-0.22 μm to obtain the first nanovesicles ingredient;

wherein the preparing of the second nanovesicles ingredient comprises the steps of:

(g1) collecting a fruit mixture including 3 parts of dragon fruit, 3 parts of avocado, and 1 part of watermelon;

(g2) washing the fruit mixture three times with deionized water at 20° C.-25° C.;

(g3) pureeing the washed fruit mixture with phosphate buffer solution (PBS) in a ratio of 1:1 (g/mL) at a speed of 7000-8000 rpm for 15 minutes to obtain a first foundation solution;

(g4) filtering the first foundation solution by a filter membrane with a diameter 0.20-0.22 μm to obtain a second foundation solution;

(g5) centrifuging the second foundation solution by ultracentrifugation at 100000×g for 60 min to obtain a residue;

(g6) dissolving the residue in phosphate buffer solution (PBS), transferring to a 45% sucrose gradient solution, and ultracentrifugation at 130000×g for 100 min to obtain a third foundation solution;

(g7) stirring the third foundation solution with a 10% polyethylene glycol-8000 (PEG8000) solution in a ratio of 1:1 v/v, and incubating for 8-10 hours at 4° C., then centrifuging at 110000×g for 40 minutes at 4° C. to obtain a precipitate;

(g8) dissolving the precipitate in phosphate buffer solution (PBS) in a ratio of 1:2 w/v to obtain a foundation solution; and (g9) filtering the foundation solution by a tangential flow filtration (TFF) to obtain the second nanovesicles ingredient; wherein the TFF comprises a molecular size of 500 kDa, and filtering at a flow rate of 20 mL/min with the transmembrane pressure maintained at 2 bar;

(ii) mixing the solution containing 4-allylpyrocatechol with the plant-derived nanovesicles ingredient at temperatures of 30° C.-50° C., with stirring at an average speed of 400 rpm for 15 minutes to obtain a solution 10;

(iii) mixing the herbal concentrate with the herbal powder mixture, the mushroom extract ingredient, the collagen extract ingredient, and the solution 10 at temperatures of 30° C.-50° C., with stirring at an average speed of 400 rpm for 15-45 minutes to obtain a foundation mixture; and (iv) creating a herbal oral composition, wherein 100 mL of the herbal oral composition created by mixing performed in a specific order from (h1) to (h3) comprising:

(h1) adding 125 mg of the foundation mixture with 100 mg of glycyrrhizic acid, 50 mg of a phospholipid component, and 315 mg of lipoid S100 into a reaction tank, adding 0.2 part of absolute ethanol, refluxing at 60° C. for 2 hours to obtain a solution 20;

(h2) dissolving 250 mg of chitosan with 10 mL of distilled water, slowly adding 0.5 mL of glacial acetic acid, combined with stirring 50 rpm, adding 30 ml of water and let stand until the solution is clear, transferring the cleared solution into a 50 mL volumetric flask, and adding distilled water to the mark to obtain 50 mL of a chitosan solution with concentration of 5 mg/mL; and (h3) dissolving 1 mL of the chitosan solution at step (h2) with 300 mg of a poloxamer component and 85 mL of distilled water, cooling the reaction mixture and stirring at 600 rpm until the reaction mixture is homogeneous, injecting 8 mL of the solution 10 at a rate of 1 mL/min with a stirring speed of 1000 rpm for 30 minutes, and adding distilled water to make 100 mL of the herbal oral composition having the properties for supporting and enhancing musculoskeletal health.

10. The herbal oral composition of claim 9, wherein the by-products from herring is selected from the one or more in the genus *Sardinella* of the including *Sardinella aurita*, *Sardinella jussieu*, *Sardinella albella*, *Sardinella atricauda*, *Sardinella brachysoma*, *Sardinella fijiense*, *Sardinella fimbriata*, *Sardinella hualiensis*, *Sardinella marquesensis*, and *Sardinella melanura*.

11. The herbal oral composition of claim 9, wherein the poloxamer component is selected from the group consisting of poloxamer 124, poloxamer 188, poloxamer 237, poloxamer 338, and poloxamer 407.

12. The herbal oral composition of claim 9, wherein the phospholipid component is selected from the group consisting of phosphatidylcholine (DMPC), phosphatidylserine (PS), and phosphatidylethanolamin (PE).

13. The herbal oral composition of claim 9, wherein the pineapple and papaya juice mixture is prepared by mixing a pineapple juice with a papaya juice in a ratio of (1-5):(1-5) v/v.

14. The herbal oral composition of claim 9, wherein said first percentage (%) by weight is between 25% to 60%, said second percentage (%) by weight is between 20% to 60%, said third percentage (%) by weight is between 0.5% to 18%, said fourth percentage (%) by weight is between 0.1% to 20%, said fifth percentage (%) by weight is between 0.01% to 0.45%, and said sixth percentage (%) by weight is between 0.02% to 0.2% of the total weight of said foundation mixture.

15. The herbal oral composition of claim 14, wherein said first percentage (%) by weight is between 30% to 60%, said second percentage (%) by weight is between 30% to 60%, said third percentage (%) by weight is between 1.5% to 18%, said fourth percentage (%) by weight is between 2.5% to 20%, and said fifth percentage (%) by weight is between 0.01% to 0.45%, and said sixth percentage (%) by weight is between 0.02% to 0.2% of the total weight of said foundation mixture.

* * * * *